(12) United States Patent
Stoppini

(10) Patent No.: US 8,927,282 B2
(45) Date of Patent: Jan. 6, 2015

(54) METHOD OF PRODUCING ORGANOTYPIC CELL CULTURES

(75) Inventor: Luc Stoppini, Geneva (CH)

(73) Assignee: Capsant Neurotechnologies S.A. (CH)

( * ) Notice: Subject to any disclaimer, the term of this patent is extended or adjusted under 35 U.S.C. 154(b) by 1309 days.

(21) Appl. No.: 11/922,268

(22) PCT Filed: Jun. 15, 2006

(86) PCT No.: PCT/IB2006/002062
§ 371 (c)(1),
(2), (4) Date: Sep. 19, 2008

(87) PCT Pub. No.: WO2006/136953
PCT Pub. Date: Dec. 28, 2006

(65) Prior Publication Data
US 2009/0042288 A1     Feb. 12, 2009

(30) Foreign Application Priority Data

Jun. 15, 2005   (GB) .................................. 0512214.8

(51) Int. Cl.
| | | |
|---|---|---|
| C12N 5/06 | (2006.01) | |
| C12M 3/00 | (2006.01) | |
| C12N 5/00 | (2006.01) | |
| C12M 1/12 | (2006.01) | |
| C12M 3/06 | (2006.01) | |

(52) U.S. Cl.
CPC .............. C12N 5/0062 (2013.01); C12M 25/02 (2013.01); C12M 23/16 (2013.01)
USPC ........ 435/395; 435/373; 435/297.4; 435/378; 435/401

(58) Field of Classification Search
CPC ...... C12N 5/0062; C12M 25/02; C12M 23/16
USPC ...................... 435/373, 325, 297.1, 401, 378
See application file for complete search history.

(56) References Cited

U.S. PATENT DOCUMENTS

| | | | |
|---|---|---|---|
| 4,154,795 A | 5/1979 | Thorne | |
| 4,324,859 A | 4/1982 | Saxholm | |
| 4,908,236 A | 3/1990 | Pitt et al. | |
| 5,284,753 A | 2/1994 | Goodwin | |
| 5,583,037 A | 12/1996 | Mussi et al. | |
| 5,834,312 A | 11/1998 | Wille, Jr. | |
| 5,958,762 A * | 9/1999 | Stoppini et al. ............ | 435/297.5 |
| 6,043,027 A | 3/2000 | Selick et al. | |
| 6,157,856 A | 12/2000 | Sanghera et al. | |
| 6,517,856 B1 | 2/2003 | Roe et al. | |
| 6,689,594 B1 | 2/2004 | Hanni et al. | |
| 7,897,377 B2 | 3/2011 | Stoppini | |
| 2004/0151729 A1 | 8/2004 | Michalopoulos et al. | |
| 2004/0175367 A1 | 9/2004 | Herlyn et al. | |
| 2005/0226784 A1 | 10/2005 | Kobayashi | |
| 2006/0160066 A1 | 7/2006 | Bhatia et al. | |
| 2009/0137032 A1 | 5/2009 | Stoppini | |
| 2010/0255528 A1 | 10/2010 | Zudaire et al. | |
| 2011/0287470 A1 | 11/2011 | Stoppini | |
| 2011/0287982 A1 | 11/2011 | Stoppini | |

FOREIGN PATENT DOCUMENTS

| | | |
|---|---|---|
| CN | 101157908 | 4/2008 |
| EP | 1078982 A2 | 2/2001 |
| EP | 1133691 | 9/2001 |
| EP | 1205541 A1 | 5/2002 |
| EP | 1367119 A2 | 12/2003 |
| JP | 02-117381 | 5/1990 |
| JP | 3147782 | 6/1991 |
| JP | 6505636 | 2/1992 |
| JP | 08-256756 A | 10/1996 |
| JP | 10506198 T | 6/1998 |
| JP | 2004344087 A | 12/2004 |
| JP | 2005502351 T | 1/2005 |
| WO | WO92/15700 | 2/1992 |
| WO | WO94/16098 | 7/1994 |
| WO | WO 96/21851 | 7/1996 |
| WO | WO 97/04074 | 2/1997 |
| WO | WO9964559 | 6/1999 |
| WO | WO 99/58042 | 11/1999 |
| WO | WO 99/64559 | 12/1999 |
| WO | WO 2004/007699 A2 | 1/2004 |
| WO | WO 2005/107642 | 11/2005 |
| WO | 2005123950 | 12/2005 |
| WO | WO 2006/134432 | 12/2006 |
| WO | WO2006/136953 | 12/2006 |
| WO | WO2010020875 | 2/2010 |
| WO | WO2010020876 | 2/2010 |

OTHER PUBLICATIONS

Bergold et al. Preparation of Organotypic Hippocampal Slice Cultures Using the Membrane Filter Method. Neurotransmitter Methods, Methods in Molecular Biology, 1997, vol. 72, 15-17.*

(Continued)

*Primary Examiner* — Taeyoon Kim

(74) *Attorney, Agent, or Firm* — Kilpatrick Townsend & Stockton LLP

(57) ABSTRACT

The present invention relates to cell and tissue culture. In particular, the present invention provides a method for preparing an organotypic culture using dissociated cells or microexplants obtained from an animal organ. The method for preparing an organotypic culture comprises culturing cells from an organ on a surface characterized in that the cells are compacted. The invention further relates to a high-throughput method for the preparation of a collection of organotypic cultures. The invention further relates to a device for carrying out a method of organotypic culture according to the invention.

37 Claims, 16 Drawing Sheets

(56) References Cited

OTHER PUBLICATIONS

Figure 3:
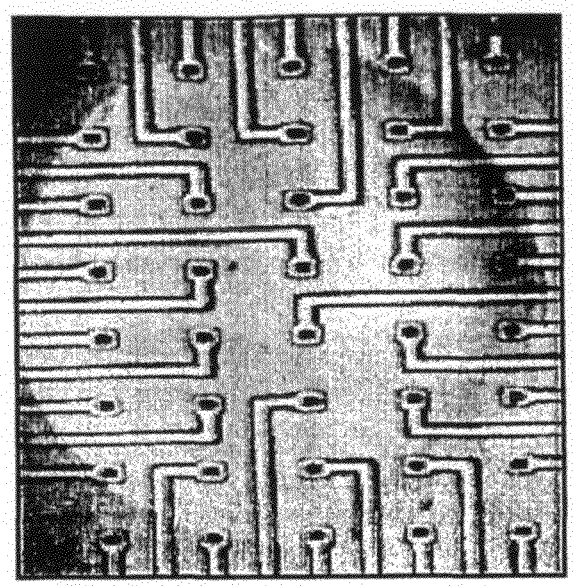

Millicell®—CM Low Height Culture Plate Inserts brochure. 2004. p. 1-8.*
Beaupain, et al., 'A method for three-dimensional coculture of cancer cells combined to any other type of cells maintained organotypically,' *Methods in Cell Science*, 21(1):2-30 (1999).
Becker-Hapak, et al., 'TAT-mediated protein transduction into mammalian cells,' *Methods*, 24:247-256 (2001).
Buchs, et al., 'Structural modifications associated with synaptic development in area CA1 of rat hippocampal organotypic cultures,' *Developmental Brain Res.*, 71:81-91 (1993).
Chatterjee, 'The effect of culture on ultrastructure of dissociated rabbit adenobypophysial cells,' *J. Anat.* 121(2):241-258 (1975).
Corradino, 'Embryonic chick intestine in organ culture. A unique system for the study of the intestinal calcium absorptive mechanism,' *J. Cell. Biol.*, 58:64-78 (1973).
Douglas, et al., 'Organotypic Culture of Dissociated Fetal Rat Lung Cells on a Collagen Sponge Matrix,' TCA (Tissue Culture Association) Manual, 4(1):749-753 (1978).
Fawcett, et al., 'Dopaminergic neuronal survival and the effects of bFGF in explant, three dimensional and monolayer cultures of embryonic rat ventral mesencephalon,' *Exp. Brain Res.*, 106:275-282 (1995).
Feng, 'Imaging neuronal subsets in transgenic mice expressing multiple spectral variants of GFP,' *Neuron*, 28:41-51 (2000).
Honegger, et al., 'Aggregating Neural Cell Cultures,' in *Protocols for Neural Cell Culture* (Federoff and Richardson, Editors) Third Edition, Humana Press, Totowa, NJ USA, ISBN 1-59259-207-4, pp. 199-218 (2001).
Kalabis, et al., 'Stimulation of human colonic epithelial cells by leukemia inhibitory factor is dependent on collagen-embedded fibroblasts in organotypic culture,' *FASEB, J.*, 17:1115-1117 (2003).
Mazurkiewicz, et al., 'Organotypic Cultures of the Avian Salt Gland Biosynthesis of Membrane Proteins,' Journal of Cell Science, 48:75-88 (1981).
Michalopoulos, et al., 'Histological organization in hepatocyte organoid cultures,' *Am. J. Pathol.*, 159:1877-1887 (2001).
Muller, et al., 'Interface Organotypic Hippocampal Slice Cultures,' *Protocols for Neural Cell Culture*, 3rd Edition, Federoff and Richardson, Editors, pp. 13-27 (2001).
Mummery, et al., 'Cardiomyocyte differentiation of mouse and human embryonic stem cells,' *J. Anat.*, 200:233-242 (2002).
Piper, et al., 'Novel SOX9 expression during human pancreas development correlates to abnormalities in Campomelic dysplasia,' *Mech. Dev.*, 116:223-226 (2002).
Ren, et al., Altered inotropic response to insulin-tike growth factor I in diabetic rat heart: influence of intracellular Ca2+ and nitric oxide, *Am. J. Physiol.*, 275:H823-H830 (1998).
Rochkind, et al., 'Transplantation of embryonal spinal cord nerve cells cultured on biodegradable microcarriers followed by low power laser irradiation for the treatment of traumatic paraplegia in rats,' *Neurol Res.*, 24:355-360 (2002).
Smith, et al., 'Measurement of protein using bicinchoninic acid,' *Anal. Biochem.*, 150:76-85 (1985).
Stoppini, et al., Lesion-induced neurite sprouting and synapse formation in hippocampal organotypic cultures, *Neuroscience*, 57(4):985-994 (1993).
Stoppini, et al., 'A simple method for organotypic cultures of nervous tissue,' *Neurosci. Methods*, 37:173-182 (1991).
Turnpenny, et al., 'Derivation of human embryonic germ cells: an alternative source of pluripotent stem cells,' *Stem Cells*, 21:598-609 (2003).
Verrill, et al., Organotypic liver culture in a fluid-air interface using slices of neonatal rat and adult human tissue —a model of fibrosis in vitro, *J. PharmacoL Toxicol. Methods*, 48:103-110 (2002).
Wicks, 'Induction of tyrosine-alphaketoglutarate transaminase in fetal rat liver,' *J. Biol. Chem.*, 243:900-906 (1968).
Wildenthal, 'Long-term maintenance of spontaneously beating mouse hearts in organ culture,' J. Appl. Physiol., 30:153-157 (1971).

Amit, M., et al., "Feed Layer-and Serum-Free Culture of Human Embryonic Stem Cells," *Biology of Reproduction* 70:837-845 (2004).
Bentz, K., et al., "Neural Differentiation of Embryonic Stem Cells is Induced by Signalling from Non-Neural Niche Cells," *Cell Physiol. Biochem*, 18:275-286 (2006).
Cavallari, et al., "Rat Pancreatic Islet Siaze Standardization by the 'Hanging Drop' Technique", Transplantation Proceedings, Orlando, FL, 39(6):2018-2020 (2007).
Dang, et al., "Efficiency of Embryoid Body Formation and Hematopoietic Development from Embryonic Stem Cells in Different Culture Systems," *Biotechnol. Bioeng.* 78:442-453 (2002).
Gerecht-Nir, "Bioreactor Cultivation Enhances the Efficiency of Human Embryoid Body (hEB) Formation and Differentiation," *Biotechnol. Bioeng.*, 86:493-502 (2004).
Guo, et al., "Engineering cardiac tissue from embryonic stem cells," *Methods Enzymol.*, 420:316-38 (2006).
Ikeda, et al. "Generation of Rx+/Pax6+ neural retinal precursors from embryonic stem cells," *Proc Natl Acad Sci USA*, 102(32):11331-6 (2005).
Keller, "In vitro differentiation of embryonic stem cells," *Curr. Opin. Cell. Biol*, 7:862-869 (1995).
Keller, "Embryonic stem cell differentiation: emergence of a new era in biology and medicine," *Genes Dev.*, 19:1129-1155 (2005).
Konno, et al., Formation of Embryoid Bodies by Mouse Embryonic Stem Cells on Plastic Surfaces, *J. Biosci. Bioeng.*, 100:88-93 (2005).
Kurosawa, et al., "A Simple Method for Forming Embryoid Body from Mouse Embryonic Stem Cells," *Biosci. Bioeng.*, 96:409-411 (2003).
Kurosawa, et al., "Methods for inducng embryoid body formation: in vitro differentiation system of embryonic stem cells" *Journal of Bioscience and Bioengineering, Elsevier Amsterdam, NL*, 103(5):389-398 (2007).
Nakano, et al., << Generation of Lymphohematopoietic Cells from Embryonic Stem Cells in Culture, *Science*, 265:1098-1101 (1994).
Oh, et al., High Density Cultures of Embryonic Stem Cells, *Biotechnol. Bioeng.*, 91:521 (2005).
Pouton, et al.,"Embryonic stem cells as a source of nodels for drug discovery" *Nature Reviews*, Drug Discovery, Nature Publishing Group, GB. 6(8):605-616 (2007).
Sundstrom, et al., "Organotypic cultures as tools for functional screening in the CNS. Drug Discov Today," *Review*, 10(14):993-1000 (2005).
Sundstrom, "Thinking inside the box. To cope with an increasing disease burden, drug discovery needs biologically relevant and predictive testing systems," *EMBO Reg.*, 8:Spec No. S40-3 (2007).
Takahashi, et al., "Induction of pluripotent stem cells from adult human fibroblasts by defined factors," *Cell.*,131(5):861-72 (2007).
Van Der Heyden, et al., Twenty one years of P19 cells: what an embryonal carcinoma cell line taught us about cardiomyocyte differentiation, *Cardiovasc. Res.*, 58:292-302 (2003).
Vanderlaan, et al., "Electrophysiologicial Profiling of Cardiomyocytes in Embryonic Bodies Derived From Human Embryonic Stem Cells," *Circulation Research*, 93:1 (2003).
Yamanaka, "Strategies and new developments in the generation of patient-specific pluripotent stem cells," *Cell Stem Cell*, 1(1):39-49 (2007).
Yang, et al., "Human cardiovascular progenitor cells develop from KDR+ embryonic-stem-cells-derived population," *Nature*, 453(7194):524-8. Epub (2008).
International Search Report dated Feb. 5, 2010 in Application No. PCT/IB2009/006726.
International Search Report dated Feb. 5, 2010 in Application No. PCT/IB2009/006725.
English translation of the Examination Report for Japanese Patent Application No. 2008-516447 (corresponding to patent publication JP6505636) dated Feb. 16, 2012.
Chung et al., Human Embryonic Stem Cell Lines Generated Without Embryo Destruction, Cell Stem Cell 2, Feb. 2008, pp. 113-117.
Smith et al., "Measurement of protein using bicinchoninic acid", Anal. Biochem, vol. 150, 1985, pp. 76-85.
Office Action dated Dec. 20, 2012 in related U.S. Appl. No. 13/060,062.

(56) References Cited

OTHER PUBLICATIONS

Office Action dated Mar. 14, 2013 in related U.S. Appl. No. 13/060,064.

Office Action Response dated Jan. 23, 2014 in related U.S. Appl. No. 13/060,064 15 pages.

Office Action dated Feb. 18, 2010 in related U.S. Appl. No. 11/922,253, 13 pages.

Office Action Response dated Aug. 18, 2010 in related U.S. Appl. No. 11/922,253, 33 pages.

Office Action dated Oct. 23, 2013 in related U.S. Appl. No. 13/060,064, 12 pages.

Office Action Response dated Jun. 11, 2013 in related U.S. Appl. No. 13/060,064, 13 pages.

Office Action dated Feb. 20, 2014 in related U.S. Appl. No. 13/060,064, 18 pages.

International Search Report and Written Opinion dated May 9, 2012 in PCT/EP2012/050194, 3 pages.

Damia et al., Contemporary pre-clinical development of anticancer agents—What are the optimal preclinical models? European Journal of Cancer, 45, 2009, pp. 2768-2781.

Harma et al., A Comprehensive Panel of Three-Dimensional Models for Studies of Prostate Cancer Growth, Invasion and Drug Responses, 5(5) PLOS ONE, 2010.

Holliday et al., Development of in vitro models to study microenvironmental influences on breast cancer progression, Breast Cancer Research and Treatment, 106 (Suppl. 1) Springer, NY, 2007, S201-S202.

Kelland, 'Of mice and men': values and liabilities of the athymic nude mouse model in anticancer drug development, European Journal of Cancer 40, 2004, 827-836.

Ridky et al., Invasive three-dimensional organotypic neoplasia from multiple normal human epithelia, Nature Medicine, 16(12), 2010, 1450-1455.

Rygaard et al., Heterotransplantation of a Human Malignant Tumour to "Nude" Mice, Acta Pathology Microbiol. Scand., 77, 1969, 758-760.

Schuldiner et al., Effects of Eight Growth Factors on the Differentiation of Cells Derived from Human Embryonic Stem Cells, PNAS, 97(21), 2000, 11307-11312.

Starzec et al., Spatial organization of three-dimensional cocultures of adriamycin-sensitive and -resistant human breast cancer MCF-7 cells, Biology of the Cell, 95, 2003, 257-264.

Vaira et al., Preclinical model of organotypic culture for pharmacodynamic profiling of human tumors, PNAS, 107(18), 2010, 8352-8356.

Van Der Kuip et al., Short term culture of breast cancer tissues to study the activity of the anticancer drug taxol in an intact tumor environment, BMC Cancer, 6(86), 2006, 1-11.

* cited by examiner

Axon detail

Axon growth between cultures

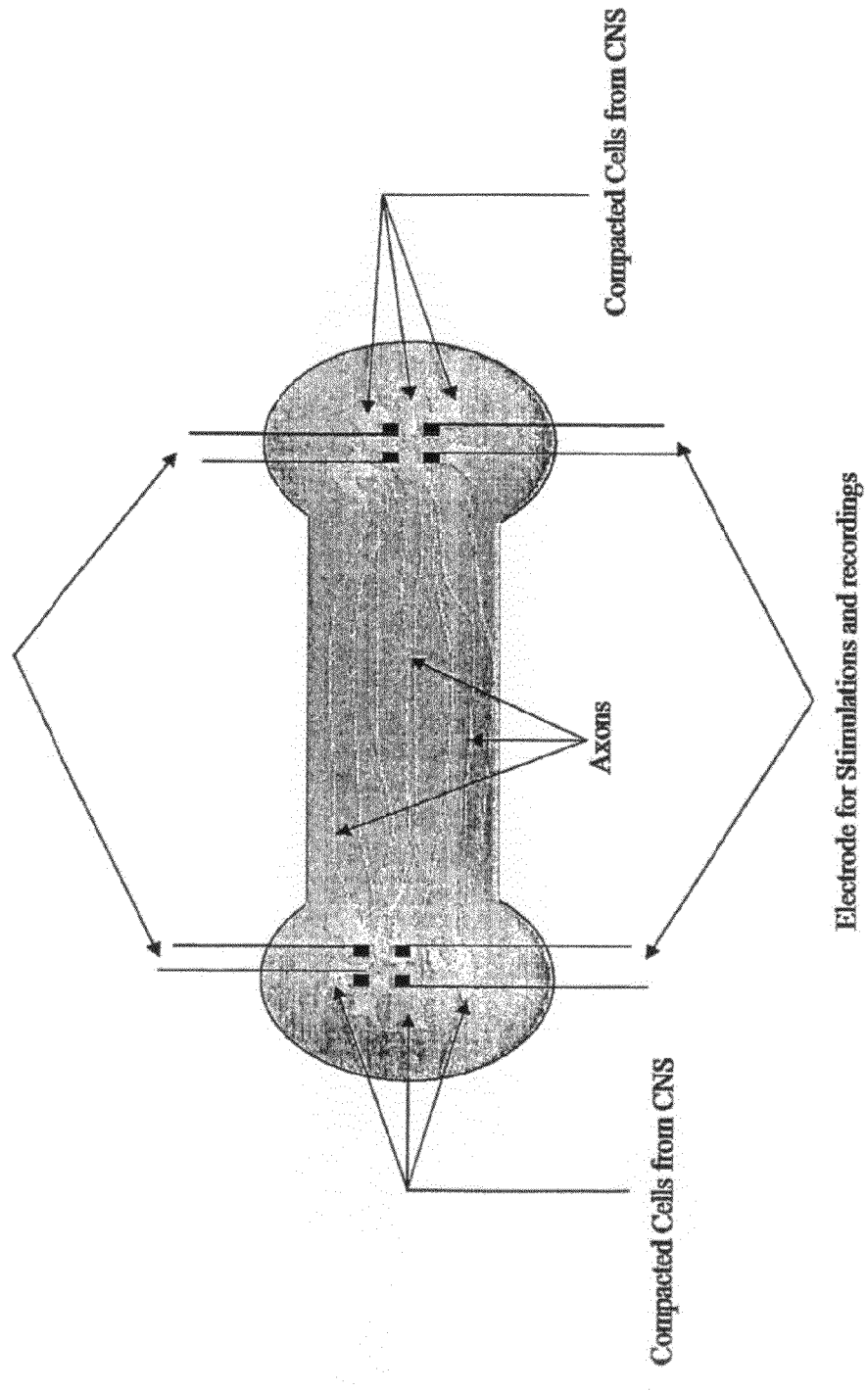

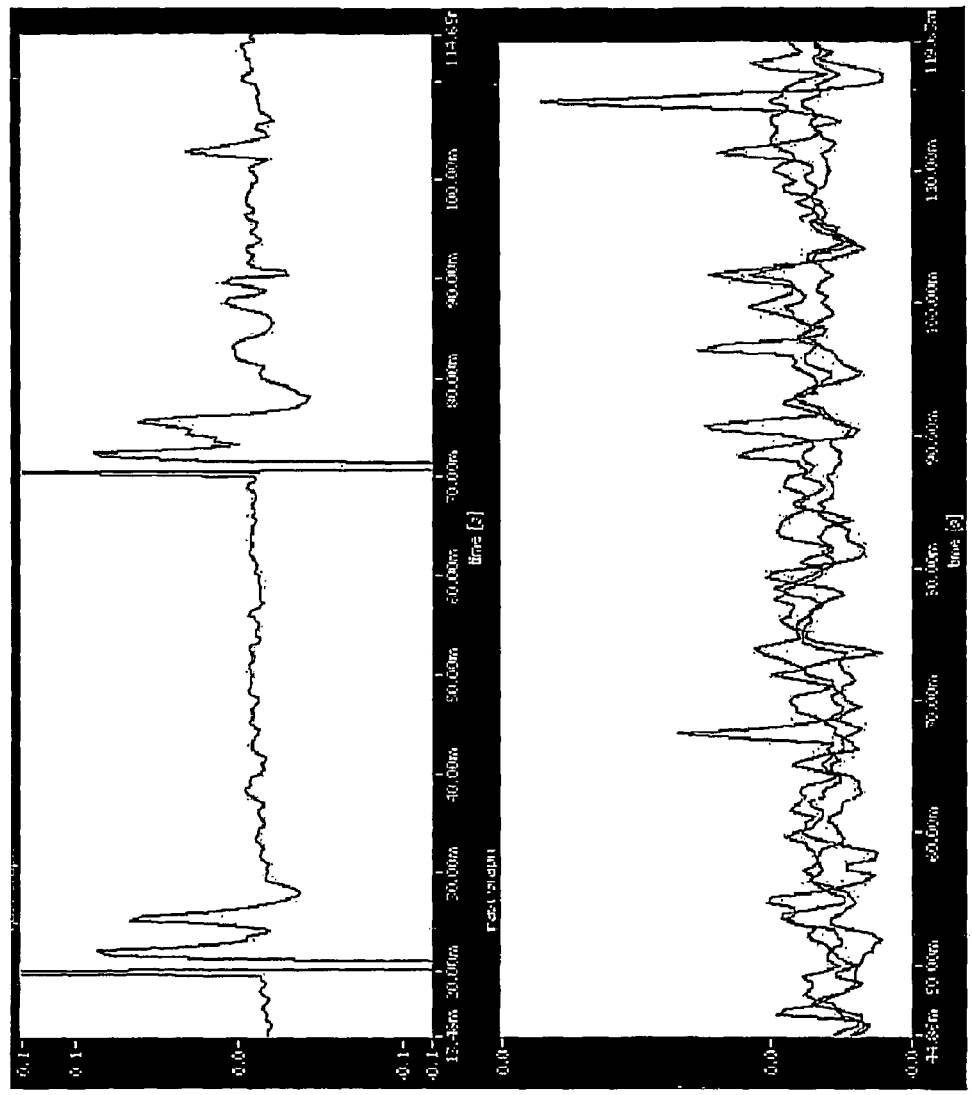

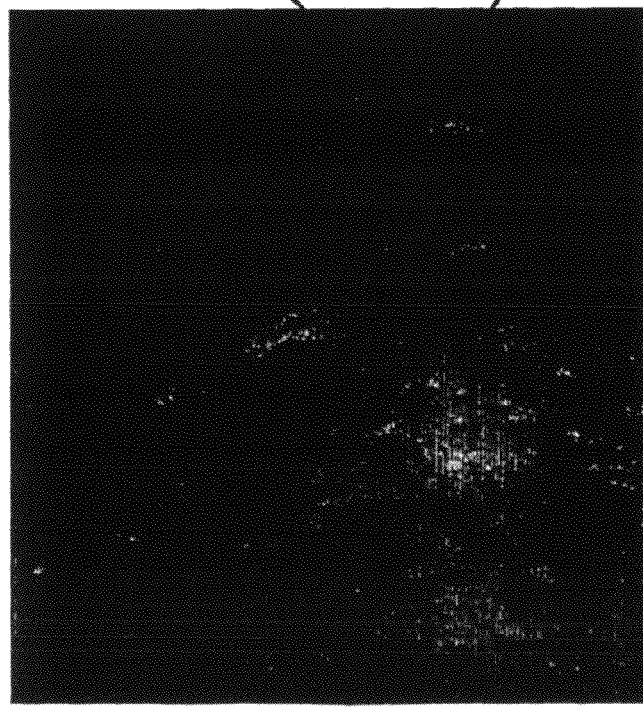
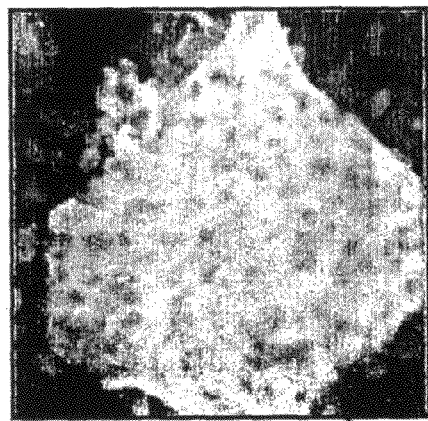
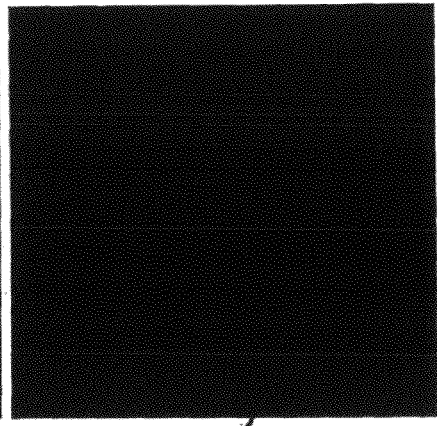
FIG. 12A
FIG. 12B
FIG. 12C

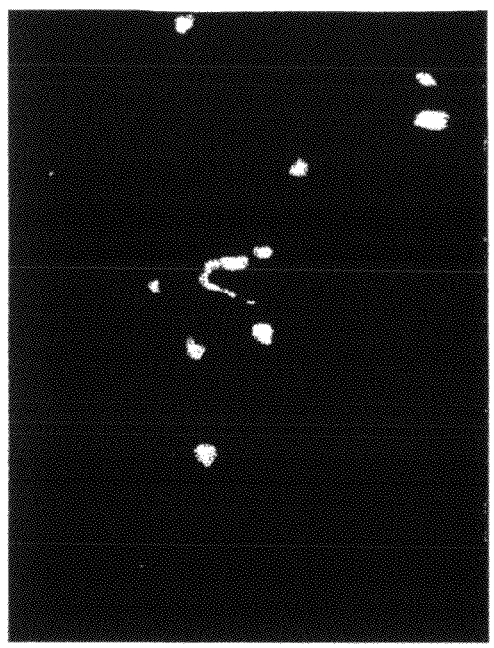
FIG. 14
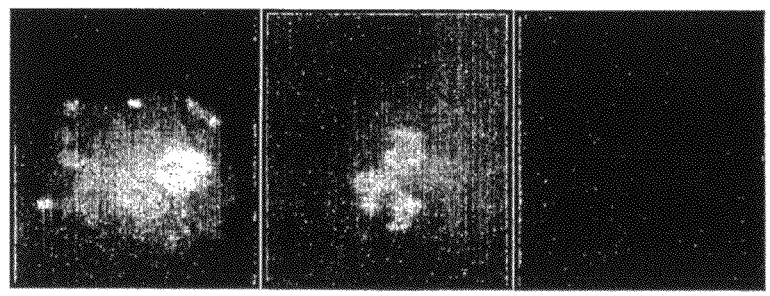
B  C  D
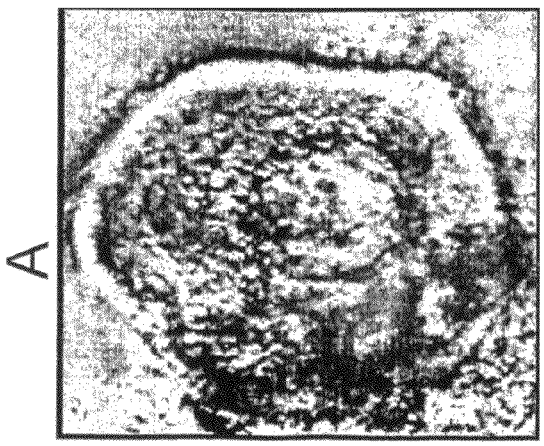
FIG. 13
A

METHOD OF PRODUCING ORGANOTYPIC CELL CULTURES

CROSS REFERENCE TO RELATED APPLICATIONS

This application is the U.S. national phase of International Application No. PCT/I82006/002062 filed on Jun. 15, 2006 and published in English on Dec. 28, 2006 as International Publication No. WO 2006/136953 A2, which application claims priority to Great Britain Patent Application No. 0512214.8 filed on Jun. 15, 2005, the contents of which are incorporated herein by reference.

The present invention relates to cell and tissue culture. More particularly, the present invention provides a method for preparing an organotypic culture using dissociated cells or microexplants obtained from an animal organ.

Tissue culture is the ex vivo maintenance of cells that originated from an organ or tissue of an animal or plant organism. Methods of tissue culture have been developed and improved over many decades.

The culture of cells obtained directly from a plant or animal organ or tissue is called primary culture. According to one method of primary culture, organ explants are placed in a suitable sterile culture medium in a suitable culture vessel provided with a sterile atmosphere of suitable composition, such that cells grow from the edges of the explant. Another approach to primary culture is to dissociate the cells of the organ or tissue by treatment with a proteolytic enzyme such as trypsin, which breaks down the proteins that cause adhesion between the cells that comprise the organ or tissue. Mechanical methods can also be used to dissociate cells of an organ or tissue, or a combination of mechanical and enzymatic methods can be used. The dissociated cells can then be cultured in an appropriate environment as described above. In cases where it is desirable to culture a particular population of cells, the dissociated cells may be fractionated, for example by density gradient centrifugation. The isolated cell population of interest is then resuspended in medium so that the cells become dissociated and the dissociated cells of that population are cultured in an appropriate environment.

One disadvantage of primary cultures of animal cells is that the cells only have a limited lifespan. Cells in primary culture may undergo cell division but they usually do so only a limited number of times before undergoing a form of cell death called senescence. A further disadvantage of explant-based animal cell primary culture is that the cultured cells usually lose many of the characteristics that are typical of cells in the source organ in vivo, unless specific steps are taken to prevent such loss of characteristics. This loss of in vivo characteristics occurs by three different routes. Firstly, all organs are mixtures of various cell types, and in primary culture one cell type may outgrow the others to dominate the culture. Secondly, one or more of the component cell types may de-differentiate to some extent, losing many of its specific characteristics. Thirdly, one or more de-differentiated or partially de-differentiated cells in the culture may become immortal, fail to senesce, and grow to become a permanent cell line. Such immortal cell lines may be cultured indefinitely, and there are many thousands of examples of immortal cell lines from virtually every organ of human and experimental animals such as rat and mouse.

The loss of in vivo characteristics during explant-based or dissociated cell-based primary culture and the emergence of immortal cell lines has major implications for biological and medical research and product development because it means that such primary cell cultures cannot be used to predict in vivo responses accurately. As a result, many biological tests to assess the safety and efficacy of candidate drugs must be carried out in vivo in whole animals. Such tests in whole animals are expensive, leading to higher healthcare costs, and may compromise animal welfare. For many years, there has therefore been considerable impetus to develop in vitro tests which more accurately predict an in Vivo response.

Organ culture is the maintenance of all or part of an animal organ ex vivo, under conditions which sustain the life and function of the organ for a period of time. For example, there are established procedures to culture liver (Wicks W., 1968), heart (Wildenthal K., 1971) and intestine (Corradino R., 1973). Organ culture has a major advantage over explant-based primary cell cultures and cell lines in that most or all of the physiological properties of the organ are maintained. However, the throughput of organ culture is limited by the manipulations necessary to remove the organ surgically from the host and set up the culture system. Furthermore, only one, two or a few cultures can be obtained per donor animal. These limitations render organ culture too slow and costly for drug screening and drug target screening, together with many other applications in biological research.

A major advance in the field of tissue culture has been the introduction of organotypic culture methods for organ and tissue slices. Thin (50-500 µm) slices of an animal organ are cultured under conditions in which the slices retain the cellular composition, morphology and the physiological properties of the source organ. The conditions in which the organ slices are cultured are critical to achieve organotypic culture. The organ slices are cultured on the upper surface of a porous membrane and supplied with nutrient from the lower surface of said porous membrane such that the organ slice is not fully immersed but is covered only by a thin film of culture medium (Stoppini L. et al, 1991). Gas transfer to the slice, both for the uptake of oxygen and the removal of carbon dioxide, is much more efficient than when the slice is fully immersed in culture medium according to the methods of explant culture. In addition, organotypic slice culture does not suffer from the disadvantages associated with explant-based and dissociated cell-based primary cultures discussed above. For example, primary culture of dissociated cells from the hippocampal region of rodent brain leads to loss of neurons and replacement by glial cells, and can only be used for neuronal studies for 2-3 days. In contrast, the organotypic slice method of hippocampal culture leads to initial migration of glial cells to the surface of the slice in contact with the membrane, but retention of neurons and in particular the retention of inte-nieuronal and glial cell-neuronal connectivity. It has been shown that new synapses develop in organotypic brain slice cultures (Buchs P. et al, 1993) and that damage to neuronal connections in organotypic brain slice cultures can be at least partially repaired by axon outgrowth and synaptic development (Stoppini L et al, 1993). There are many examples of organotypic culture of slices of other tissues based on the same principles and there have been suggestions for improving methods of culturing a single organotypic slice. For example, Giehl (2002) discloses the use of aspiration to reduce the degree of surface wetting of organotypic slices from older animals.

Organotypic slice culture is significantly faster and more flexible than organ culture, but it is still too slow and expensive for the large-scale screening needed for drug discovery. The procedures used to dissect organs from animals or to process post-operative human material are labour-intensive, and it is possible to carry out only tens of cultures in parallel in most laboratories. For drug screening, it would be far more useful to provide thousands, tens of thousands or hundreds of thousands of cultures in parallel. Furthermore, organ slices are relatively refractory to the use of transfected or transduced vectors for transgene or small interfering RNA (siRNA) expression, or the use of oligoribonucleotides directly for siRNA ablation of gene expression. Usually only the surface layers of the slice are efficiently transfected or transduced, and overall transfection or transduction efficiencies are usually in the range of 10-30% of the cells in the slice. This is often inadequate to assess the biological effects of transgene expression or siRNA-induced ablation of gene expression.

In view of the disadvantages associated with organotypic slice culture, efforts have been made to develop methods of producing organotypic cultures using dissociated cells from a particular organ instead of organ slices.

One approach to the development of organotypic cultures from dissociated cells has been to use extracellular matrix proteins to encourage dissociated cells to migrate into appropriate layers or zones and to re-form functional cell-cell interactions in the presence of appropriate growth factors. This approach has been used in the preparation of organotypic liver cultures (Michalopoulos G. et al, 2001; Michalopoulos G. and Bowen W., 2004). Similarly, artificial matrices have been used as "scaffolds" for the organisation of neuronal cells grown in suspension, enabling the growth of cell aggregates that are potentially useful as implants to treat disease (Rochkind S. et al, 2002; Shahar A. et al, 2001). Epithelial tissues have been a particular focus of research and it has been shown that a protein matrix can be used to encourage dissociated intestinal epithelial cells to form an organotypic culture (Kalabis J. et al, 2003; Herlyn M., 2004). There have been a number of similar approaches to the organotypic culture of skin epithelium, which is important for grafting after skin injury. However, these methods are not ideal due to their reliance on matrix proteins which are expensive and complex to use due to the need to build a 3D structure of matrix proteins before setting up the culture.

A couple of culture methods have been developed which are not reliant on the use of matrix proteins. For example, it has been found that rotation-mediated aggregation of dissociated neuronal cells can be used to form so-called "neurospheres" (Honegger, P., and Monnet-Tschudi, F., 2001). It has also been found that stem cells from the basal layer of stratified epithelium, isolated by culture from dissociated epithelium as a result of their ability to proliferate, can be induced to differentiate in a step-wise process to create stratified and cornified epithelium using specific growth factors (Wille J., 1998). However, this process is specific for stratified epithelium, and requires the use of purified growth factors that are appropriate for the differentiation of stratified epithelium.

Despite the extensive research that has been conducted to date, there is still a need for a simple, inexpensive and flexible method for the culture of organotypic tissue which is applicable to a wide variety of tissues and is suitable for the generation of thousands of parallel cultures for high-throughput screening.

SUMMARY OF THE INVENTION

According to a first aspect, the present invention provides a method of producing an organotypic culture, the method comprising culturing cells from an organ on a surface, said method being characterised in that the cells are compacted.

By "organotypic culture" is meant that the cells associate in a way that as closely as possible replicates the biochemical and physiological properties of the organ from which the cells are derived.

Preferably the cells are dissociated cells, microexplants or explants. As used herein, the term "dissociated cell" refers to a single cell that has been isolated from the organ. The term "microexplant" refers to a small group of up to 500 cells isolated from the organ. The term "explant" refers a larger group of greater than 500 cells isolated from the organ. The method of the invention involves the compaction and culture of more than one dissociated cell, or of more than one microexplant, or of more than one explant. Preferably, the method of the invention involves the compaction and culture of many dissociated cells, or many microexplants, or many explants isolated from an organ.

Preferably, the surface on which the cells are cultured is a membrane, preferably a porous membrane. Where the compacted cells are cultured on one surface of a porous membrane, the method preferably comprises supplying the contralateral surface of said membrane with nutrients. Preferably, the nutrients supplied to the contralateral surface of said membrane are in liquid form and the method thus involves supplying the contralateral surface of the membrane with liquid medium. In this embodiment, the cells on the membrane are not immersed in the liquid medium but are covered only by a thin film of culture medium allowing better gas exchange between the medium and the cells, as described, for example, by Stoppini L. et al (1991). The membrane therefore preferably has sufficient porosity for liquid media to permeate the membrane and reach the compacted cells on the opposite surface. Examples of suitable membranes are provided herein. Preferably, the liquid medium is retained in contact with the contralateral surface of the membrane by capillarity. Suitable devices that enable a volume of liquid media to be retained by capillarity are described herein.

Surprisingly, it has been found that the culture conditions described in the art for the production of organotypic cultures from organ slices (see, for example, Stoppini L. et al, 1991) can in fact be used to produce organotypic cultures from cells from organs, particularly dissociated cells, microexplants and explants, provided that the cells have been compacted so that they are densely packed together. Compacted cells will spontaneously reorganize into a complex 3-D functional parenchyma over time. For example, compacted brain cells will lead to the formation of a tissue-like structure, in which much of the appropriate synaptic circuitry, physiology and neurotransmitter receptor distribution of the intact central nervous system region are present. Functional activities of neurons in the culture are similar to their counterparts in brain and in organotypic slice cultures.

Unlike the prior art methods for producing organotypic cultures from dissociated cells, the method of the invention does not require the use of biomolecular or synthetic scaffolds. Furthermore, the cultures produced by most prior art methods only display organotypic features for 3-5 days. In contrast, the organotypic cultures produced according to the method of the invention display organotypic feature for weeks or months.

The invention thus provides a simple method of generating organotypic cultures using cells, in particular dissociated cells, microexplants or explants, from a wide variety of organs that can be maintained for several weeks or months. The fact that the organotypic cultures are easy to produce and maintain makes them ideal for the construction of many thousands of parallel cultures from a single organ for high throughput screening of drug candidates. Furthermore, the dissociated cells can be genetically manipulated efficiently prior to setting up the organotypic culture, introducing one or more transgenes by means of transfection or transduction in an appropriate vector, or by introducing siRNA as oligonucleotide or expressed from a suitable vector.

As used herein, the term "compacted" means that the cells have been subjected to a compaction force that has forced them together so that they are densely packed. Although the Applicant does not wish to be bound by theory, it is believed that it is the cell-cell contact resulting from compaction that induces organotypic growth.

Living cells do not behave as rigid bodies, but as substantially incompressible bodies. They deform and adapt their surfaces to adhere to one another, but their volume remains substantially constant unless they lose fluid. If sufficient compactive force is applied, 100% close packing will be achieved, i.e. the cells will be fully close packed with all cell membranes in contact with those of a neighbouring cell. 100% close packing is the maximum number of cells per unit volume for a given cell size without pressurizing them to the point where they lose fluid. It has been found that a culture of cells, microexplants or explants according to the present invention functions as an organotypic culture if the average degree of close packing between the elements that comprise that culture, is at least approximately 10%, more preferably 5%.

Preferably, the cells in the method of the invention are compacted to achieve between 5% and 100% close packing according to the definition of close packing described herein. Preferably, the cells are compacted to achieve greater than 5% close packing, preferably greater than 10%, 20%, 30%, 40%, 50%, 60%, 70%, 75%, 80%, 85%, 90%, 95%, 97%, 98% or 99% close packing as defined herein.

Where the method of the invention employs dissociated cells, the approximate degree of close packing may be calculated using the formula $$\text{Degree of close packing} = (N_e \times V_e / V_{cm}) \times 100\% \quad \text{(Formula 1)}$$

where
  $N_e$ is the number of cells,
  $V_e$ is the average volume of the cells, and
  $V_{cm}$ is the measured volume of the total volume of the cell mass in the culture.

Thus, 50% close packing is obtained if the measured total cell volume in the culture is twice the volume of the sum of the average cell volumes. 10% close packing is obtained if the measured total volume of the cell mass is ten times the volume of the sum of the average cell volumes. Methods for determining the number of cells ($N_e$), the average volume of the cells ($V_e$) and the volume of the total volume of the cell mass ($V_{cm}$) are described in more detail below.

Formula 1 provides a good approximation of the degree of close packing when dissociated cells isolated from an organ are used in the method of the invention. Formula 1 does not, however, provide such a good approximation of the degree of close packing of explants and microexplants. The sizes of explants and microexplants can vary from a few cells to several thousand cells. The cells that comprise each explant or microexplant are already 100% or nearly 100% close packed, but the degree of cell surface contact between cells on the surfaces of explants or microexplants that are neighbouring after compaction may be significantly less than 100%. The larger the explants or microexplants are, the less the impact of these surface contacts on the measured degree of close packing according to Formula 1, although their impact on the ability of the explants or microexplants to behave as a single organotypic culture is profound.

One way to overcome this problem might be to measure cell surface contact between microexplants and explants to determine the degree of close packing of these elements. However, methods of measuring cell surface contact are difficult and imprecise, relying on high magnification microscopic examination and subjective judgement. The difference in volume between the mass of the culture and the sum of the volumes of the component explants or microexplants is therefore used instead as an effective measure of the spaces between cell surfaces that are removed by compaction forces according to the invention. It is convenient to measure this difference in volume to determine the degree of packing of explants or microexplants because, unlike cell surface contact, explant or microexplant number and volume measurements can be obtained relatively simply and rapidly, as described below.

The degree of close packing of explants and microexplants may therefore be estimated by expressing the volume of the cells in the explants or microexplants that are capable of making new contacts as a proportion of the total space that they actually occupy in the cultured cell mass. The degree of close packing of microexplants or explants may thus be measured by the formula $$\text{Degree of close packing} = ((N_{nc} \times V_{nc} \times P_{nc}) / ((N_{nc} \times V_{nc} \times P_{nc}) + (V_{cm} - (N_e \times V_e)))) \times 100\% \quad \text{(Formula 2)}$$

where
  $N_{nc}$ is the number of cells that are capable of making new contacts,
  $V_{nc}$ is the average volume of the cells in the culture that are capable of making new contacts,
  $P_{nc}$ is the average proportion of the surface area of the cells that are capable of making new contacts that is actually available for making new contacts,
  $V_{cm}$ is the measured total volume of the cell mass in the culture,
  $N_e$ is the number of elements in the culture (cells, explants or microexplants) and
  $V_e$ is the average volume of the elements (cells, explants or microexplants) in the culture.

In the case of dissociated cells, all cells in the culture are capable of making new contacts over their entire surfaces, and therefore $N_{nc} = N_e$, $V_{nc} = V_e$ and $P_{nc} = 1$. Thus, in the case of dissociated cells, Formula 2 is equivalent to Formula 1.

Formulas 1 and 2 may be used to approximate the degree of close packing of culture elements in a culture comprised of cells, explants or microexplants of any size. 100% close packing means that there are no spaces between the elements that comprise the cell mass, whether these elements are cells, explants or microexplants.

50% close packing means that the total volume of the spaces between the elements that comprise the cell mass equals the sum of the relevant proportion of the volumes of the cells that are capable of making new contacts. In the case of dissociated cells, all cells are capable of making new contacts over their entire surfaces and so the sum of the volumes of cells that are capable of making new contacts is equivalent to the sum of the volumes of the cells that comprise the cell mass. When the culture elements are explants or microexplants, only the cells at the surfaces of the explants or microexplants are capable of making new contacts and only over approximately 50% of their surfaces. Therefore 50% close packing means that the total volume of spaces between the explants or microexplants is equal to half the sum of the volumes of the cells that are capable of making new contacts.

10% close packing means that that the total volume of the spaces between the elements that comprise the cell mass is 10 times the sum of the relevant proportion of the volumes of the cells that are capable of making new contacts. In the case of dissociated cells, this is equivalent to 10 times the sum of the volumes of the cells that comprise the cell mass. When the culture elements are explants or microexplants, 10% close packing means that the total volume of spaces between the explants or microexplants is five times the sum of the volumes of the cells that are capable of making new contacts.

The empirical measures needed to calculate the approximate degree of close packing according to Formulas 1 and 2 are the $N_e$, $V_e$, and $V_{cm}$. Formula 2 additionally requires the empirical measures $N_{nc}$, $V_{nc}$, and $P_{nC}$.

For dissociated cells, cell number ($N_e$) and cell volume ($V_e$) may be measured using the Coulter Counter marketed by Beckman Coulter Inc. This instrument uses the electrical sensing zone technique to measure both cell volume and cell number. The average volume ($V_e$) and number ($N_e$) of dissociated cells may be conveniently measured in suspension prior to compaction. Measurement of the volume of the total cell mass in culture ($V_{cm}$) following compaction then allows direct calculation of the degree of close packing according to Formula 1.

To calculate $V_{cm}$, the shape of the cultures described in the examples may be modelled. A typical organotypic culture according to the present invention is the shape of a spherical cap of diameter 5000 μm and depth 100 μm. A spherical cap is a portion of a sphere cut off by a plane, and the volume of a spherical cap can be calculated according to the formula $(\pi/6)(3r^2+h^2)h$ where r=the radius of the base and h=the height. Thus, a typical culture has a total volume of $9.8 \times 10^8$ μm$^3$. A convenient means to measure the total volume of the cell mass in the culture is to measure the diameter of a sample of cultures using a graduated eyepiece with an inverted microscope at low magnification and to measure their depth by counting the required number of confocal sections of known depth to span the full depth of the culture. The aforementioned formula may then be used to calculate the volume of the spherical cap.

Other methods for measuring the number of elements in the culture ($N_e$), the average volume of elements in the culture ($V_e$) and total volume of the cell mass ($V_{cm}$) that may be used involve the use of graduated microscope eyepieces and the use of image analysis based on pixel counting. The use of confocal microscopy also enables accurate counting in multiple fields of known depth.

Methods based on microscopy and image analysis may be used to determine the number and average volume of dissociated cells, or of cells within explants or microexplants, as well as the numbers and volumes of the explants and microexplants themselves. The magnification needed for examining single cells is obviously generally higher than that needed for examining explants and microexplants. Cell volume may vary between different individual cells in a population of cells even when these cells are of the same type, so the number and volume of cells in a given area of a microscope field of view may vary. Similarly the number and size of explants and microexplants can vary between different fields of view when examining one preparation, and between different preparations. Preferably, explant or microexplant number and volume may be measured directly prior to compaction using a graduated eyepiece with an inverted microscope at a suitable magnification and a plastic or glass needle for manipulation. The number and volume of an appropriate sample of explants or microexplants is measured in randomly chosen microscope fields of known size. It is then a simple matter to calculate the average number and dimensions of cells or groups of cells in a known volume of liquid or cell mass.

Where a mixture of different dissociated cells are used, 100% close packing is defined as the sum of all cell volumes in a mixture of cells. The total volume of a mixed population of 100% close packed cells is equal to the average cell volume multiplied by the number of cells. The average cell volume can thus be obtained by measuring the dimensions of an appropriate sample of cells and calculating the volume of each cell. Where a small proportion of cells of atypical dimensions may have a substantial effect on the calculation of average volume it will be necessary to measure the dimensions of a sufficiently large sample of cells to ensure that these cells of atypical dimensions are not excluded by sampling error.

If the volume of a cell or cell mass cannot be measured directly by the electrical sensing zone technique or another direct method, then the volume of a cell, a microexplant or explant may be calculated from its dimensions. For the purposes of the present invention, it is sufficient to approximate the shape of the cell, explant or microexplant. For example, if the shape of a cell or group of cells is approximately cuboid, then the volume of the said cell or group of cells can be calculated according to the formula $V_{cm}=L_1 \times L_2 \times L_3$, where $L_1$, $L_2$ and $L_3$ are the measured dimensions of the approximately cuboid cell or group of cells along its three principle mutually perpendicular axes. As a further example, if the dimensions of an elipsoid cell type are 12 μm in length, 8 μm in breadth and 5 μm in depth the volume of such a cell would be 2010 μm$^3$, according to the well-known formula for calculation of the volume of an elipsoid: $4/3 \times \pi \times L_1 \times L_2 \times L_3$ where $L_1$, $L_2$ and $L_3$ are the measured dimensions of the approximately elipsoid cell along its three principle mutually perpendicular axes. For cells or groups of cells of complex shapes, there are computer algorithms for calculating volume from a number of dimensions. The average volume of an appropriate number of cells, explants or microexplants may then be calculated.

It will be appreciated that for dissociated cells $N_e = N_{nc}$, $V_e = V_{nc}$ and $P_{nc} = 1$, and that $N_e$ and $V_e$ can be either measured directly or measured indirectly and calculated by the methods described above. For explants and microexplants, $N_e$ and $V_e$ may be measured directly or measured indirectly and calculated by the methods described above. The approximate average volumes $V_{nc}$ of cells at the surface of an explant or microexplant, which are those cells capable of making new cell-cell connections, may be also be simply calculated from the average dimensions of the cells in the explant or microexplant.

$P_{nc}$, the average proportion of the surface area of the cells that are capable of making new contacts that is actually available for making new contacts, for explants and microexplants is a function of the shape of cells at the surface of an explant or microexplant and the proportion of their surface area which is available for the formation of new cell-cell contacts. This value may be determined by microscopy. Based on observations of cultures produced according to the invention, it is estimated that $P_{nc}$ is generally 0.5, i.e. approximately half of the surface area of cells that are capable of making new contacts are actually available for making new contacts.

$N_{nc}$, the number of cells at the surface of explants and microexplants of average volume, may be estimated from $V_{nc}$ and the average dimensions of the explants or microexplants. For example, assuming that the explants or microexplants and the cells that comprise them are approximately cuboid, and the explant or microexplant of the measured and calculated average volume has dimensions length $L_{x1}$, breadth $L_{x2}$ and thickness $L_{x3}$, and the component cell of the measured and calculated average volume has dimensions length $L_{y1}$, breadth $L_{y2}$ and thickness $L_{y3}$, then the estimated average number of cells at the surface of an explant or microexplant is the estimated surface area of the explant or microexplant excluding the surface layer of cells as a fraction of the estimated area of the average contact surface of each cell in the surface layer. For this approximation, the thickness of the cells on the surface layer is subtracted from the explant or microexplant dimensions to derive the estimated surface area excluding the surface layer. $N_{nc}$, the number of cells at the surface of explants and microexplants of average volume, may then be calculated according to the formula:

$$N_{nc} = ((2 \times ((L_{x1} - 2L_{y3}) \times (L_{x2} - 2L_{y3}))) + \quad \text{Formula 3}$$
$$(2 \times ((L_{x1} - 2L_{y3}) \times (L_{x3} - L_{y3}))) +$$
$$(2 \times ((L_{x2} - 2L_{y3}) \times (L_{x3} - L_{y3})))) / ((L_{y1} \times L_{y2})$$

It will be obvious to those skilled in the art that the volumes of cells of different dimensions and shapes and the volumes of cultures of different dimensions and shapes may also be calculated by the use of a variety of measuring devices and the application of the appropriate formulae or computer algorithms.

According to our measurements, the degree of compaction of organotypic cultures can be between approximately 6% and 100%. A functioning organotypic culture made according to the invention containing 10,000 dissociated cells with an average cell volume of 520 $\mu m^3$ can occupy a space as large as $9 \times 10^7$ $\mu m^3$. This equates to 5.8% compaction. A functioning organotypic culture made according to the invention containing 20,000 dissociated cells with an average cell volume of 14,000 $\mu m^3$ can occupy a space as small as $28.1 \times 10^7$ $\mu m^3$. This equates to 99.6% compaction.

The cells, preferably dissociated cells, microexplants or explants, may be compacted by any known means in order to achieve the preferred degree of close packing. The compactive force applied is sufficient to bring the cells into close contact to reach the desired level of close packing without causing cell damage. Preferably, the compactive force applied to the dissociated cells, or to the cells within the explants or microexplants is less than $2 \times 10^{-3}$ dyne per cell to avoid damage to the cells, more preferably between $10^{-5}$ dyne per cell and $5 \times 10^{-4}$ dyne per cell.

Preferably, the cells are compacted by gravitational, hydrodynamic or hydrostatic forces. Preferably, the cells are compacted by a gravitational field applied by centrifugation. The cells may also be compacted by aspiration. A combination of more than one mechanism of compaction may also be used. For example, the cells may be compacted by centrifugation and then subsequently by aspiration.

Where the cells are compacted by centrifugation, cells in suspension, whether the cells are in the form dissociated cells, microexplants or explants, are preferably compacted by centrifugation at 100-5000 g, which applies a force in the preferred range of between $10^{-5}$ dyne per cell and $5 \times 10^{-4}$ dyne per cell.

Where the cells are compacted by aspiration, cells in suspension may be placed on one side of a surface and suction applied to the opposite side of the surface to bring the cells toward that surface. The surface on which the cells are placed must be adapted to allow the suction applied to one side of the surface to be effective in compacting the cells on the other side of the surface. A pump may be used to apply a hydrodynamic force to drive fluid flow through the surface, and in this case the pump would be placed on the same side of the surface as the cells to be compacted.

The cells may be compacted before or after transfer to the surface on which they are cultured. According to a first embodiment of the first aspect of the invention, the cells are compacted before transfer to the surface for culture. There is therefore provided a method of producing an organotypic culture comprising:

i) compacting cells, preferably dissociated cells, explants or microexplants, from an organ;
ii) transferring said compacted cells to a surface; and
iii) culturing said compacted cells under suitable conditions to form an organotypic culture.

As discussed above, compaction of the cells may be carried out by centrifugation, aspiration or any other means known to the skilled person. Preferably, the cells are compacted by centrifugation, as described above. This method differs from existing methods of harvesting trypsinised cells during normal passaging since existing methods require resuspension of centrifuged cells in medium, and thus dissociation, before they are plated out. In this first embodiment of the first aspect of the invention the pellet produced by centrifugation of the cells is transferred to the surface for culture following centrifugation. According to a second embodiment of the first aspect of the invention, compaction of the cells by centrifugation and transfer of the cells to the surface are carried out simultaneously. It is advantageous in this second embodiment to provide a conduit to hold the cell suspension in the correct orientation with respect to the surface for compaction by a gravitational field. The optimum orientation is with the surface distal to the cell suspension from the point of minimum gravitational field strength. In the case of a gravitational field generated within a centrifuge, the surface is placed distal to the axis of rotation of the centrifuge rotor compared to the cell suspension. Preferably at the junction of the conduit and the surface is provided a seal between the surface and the edge of the conduit that is adjacent to the said surface, to ensure that the cells are transferred efficiently to the said surface and not lost from the conduit.

The method of the first and second embodiments of the first aspect of the invention may comprise a step of further compacting the compacted cells following transfer to the surface. This further compaction step may be carried out by any one of the mechanisms described above. For example, the compacted cells may be transferred to one side of the surface and then further compacted by the application of an aspirating force to the other side of the surface.

Preferably, the cells are further compacted following transfer to the surface by a hydrostatic force produced by capillarity. According to this preferred embodiment, the surface on which the cells are cultured is preferably a porous membrane and the contralateral surface of said membrane is supplied by liquid medium that is retained in contact with the membrane. The liquid medium is thus drawn through the pores in the membrane by capillarity and the capillarity exerted by the pores in the membrane acts to compact the cells further by hydrostatic force. The cells are thus further compacted by capillarity exerted by liquid media held on the contralateral side of the membrane. Preferably, the liquid media is held on the contralateral side of the membrane by capillarity.

In another embodiment, the cells may be compacted only after transfer to the surface. According to a second embodiment of the first aspect of the invention, there is provided a method of producing an organotypic culture comprising:

i) transferring cells, preferably dissociated cells, explants or microexplants, from an organ to a surface;
ii) compacting said cells on said surface; and
iii) culturing said compacted cells under suitable conditions to produce an organotypic culture.

The cells may be compacted on the surface by centrifugation or aspiration, or any other mechanism, as described above. The method according to this embodiment may comprise several compaction steps. For example, the dissociated cells transferred to the surface may be compacted by centrifugation on the surface and subsequently by aspiration.

Where the surface to which the compacted cells are transferred is a porous membrane, the further compaction step is preferably effected by capillarity. Preferably, the further compaction step is effected by capillarity exerted by liquid held on the contralateral side of the membrane to the compacted cells. Preferably, the liquid is a liquid medium containing nutrients required for organotypic growth of the cells. Preferably, the compacted cells are transferred to one surface of the porous membrane, liquid medium is supplied to the contralateral surface of the porous membrane and the liquid is held at the contralateral surface of the membrane by capillarity, resulting in further compaction of the cells on the opposite side of the membrane, ensuring that the cells adhere to and flatten onto the membrane.

According to a preferred method of the invention, cells from the organ are compacted by centrifugation, transferred to one side of a porous membrane and are compacted further by capillarity by the liquid medium supplied to the contralateral side of the porous membrane. A device suitable for retaining the liquid medium on the contralateral side of the porous membrane to further compact the cells by capillarity is described herein. According to a further preferred method of the invention, cells are compacted directly on one surface of the porous membrane by centrifugation and are compacted further by capillarity by the liquid medium supplied to the contralateral side of the porous membrane. A device suitable for retaining the cell suspension on one side of the porous membrane before and during centrifugation and for retaining the liquid medium on the contralateral side of the porous membrane to further compact the cells by capillarity is described herein.

Preferably, the methods of the invention further include the preliminary step of isolating the cells from the organ.

Methods for isolating dissociated cells from organs are known in the art. The dissociated cells may be isolated from the organ of interest by mechanical or enzymatic dissociation of tissue, or both. For example the dissociated cells may be obtained by dissociation of the organ using the proteolytic enzyme trypsin 0.25% (w/w) in Hank's Balanced Salt Solution (HBSS) without calcium and magnesium. After the addition of trypsin inhibitor to stop the enzymatic dissociation, the cells may be incubated briefly in suspension to allow undissociated cells to fall to the bottom, leaving the dissociated cells in suspension.

These dissociated cells may then be compacted as described above. For example, the dissociated cells in suspension may be aspirated to a fresh centrifuge tube and compacted by centrifugation at 200-1000 g for 1-5 minutes. Following aspiration of the supernatant, the cell pellet containing the compacted dissociated cells may be removed from the tube with a suitable implement, such as, for example, a disposable pipette tip and placed directly onto a surface for culture, such as a porous membrane. Alternatively, the dissociated cells in suspension may be placed directly onto a suitable surface, and the surface and cells centrifuged to compact the cells. In this embodiment it is advantageous to provide a conduit to hold the cell suspension in the correct position and orientation with respect to the surface for compaction by centrifugation. The surface is placed distal to the axis of rotation of the centrifuge rotor compared to the conduit containing the cell suspension. In a preferred embodiment at the junction of the conduit is provided a seal between the surface and the edge of the conduit that is adjacent to the said surface, to ensure that the cells are transferred efficiently to the said surface and not lost from the conduit.

The microexplants and explants used in the method of the invention may be obtained by mechanical reduction of the organ of interest to small pieces of tissue. For example, the microexplants may obtained by repeated aspiration, usually of post-natal tissue, in a disposable pipette tip, or by maceration with a scalpel blade. Preferably, the tissue is neonatal tissue.

The methods of the invention may be used to produce an organotypic culture from a wide variety of organs and the nature of the cells that are used in the process will depend on the organotypic culture that is desired. Preferably, the organ from which the cells are obtained is an animal organ, preferably a mammalian organ, preferably a human organ.

The cells may be obtained from any organ in the animal including, but not limited to the central nervous system, bone marrow, blood (e.g. monocytes), spleen, thymus heart, mammary glands, liver, pancreas, thyroid, skeletal muscle, kidney, lung, intestine, ovary, bladder, testis, uterus or connective tissue. Preferably, the dissociated cells, explants or microexplants are from the central nervous system, heart, liver or kidney. Where the dissociated cells, explants or microexplants are from the central nervous system, they may be from the brain or from the spinal cord. Preferably, the cells are from the brain, preferably from the hippocampus or the cortex. Where dissociated cells are used, they may also be stem cells. Stem cells are pluripotent cells that can be induced to differentiate, and some stem cells are capable of differentiation into multiple cell lineages. Embryonic stem cells can in principle differentiate into any cell type. Where embryonic stem cells are used, they are preferably not human embryonic stem cells.

The cells may be obtained from a particular region of the organ. For example, where the organ is brain, the cells may be obtained from the hippocampus or from the cortex. As demonstrated in the examples herein, dissociated cells from the cortical region can be used to produce an organotypic culture that shows the typical cell composition and intercellular connections of hippocampus. Where the organ is heart, the cells may be obtained from the myocardium. As shown in the examples, dissociated myocytes cultured according to the method of the invention form an organotypic culture with tight intercellular junctions and many of the physiological characteristics of heart tissue, including rhythmic coordinated contractions analogous to those of the beating heart.

The cells may be obtained from more than one organ and cultured together. For example, the cells may be derived from two, three, four or more different organs. The co-culture of cells obtained from more than one organ allows the generation of models of interactions of tissues derived from different organs. Preferably, where cells from more than one organ are used, the organs will be organs that naturally exist in contact in vivo so that the organotypic culture resulting from co-culture of cells from these organs will provide a model for the in vivo situation. For example, immune cells, particularly white blood cells, could be co-cultured with cells from various organs to study inflammation. Tumor cells might also be co-cultured with cells from various organs to study cancer development. Stem cells could be co-cultured with other cell types to produce mixed cultures. Skeletal muscle cells could be co-cultured with cells from the central nervous system, including hippocampus, cortex, cerebellum and spinal cord, to produce a model of a neuro-muscular junction. Endothelial cells that line blood vessels could be co-cultured with brain cells to form a model of the blood-brain barrier.

Where cells obtained from a variety of organs are cultured together, the method of the invention may involve compacting a mixture of the cells from the different organs (whether they are dissociated cells, microexplants or explants) and culturing the compacted mixture. It may be advantageous in particular cases to ensure that different cell types are distributed randomly within the culture. In other cases it may be advantageous to form layers of different cell types so that each cell type is in a substantially separate layer. When it is advantageous to form layers of different cell types, it may be advantageous in some further cases to ensure that one or more layers of one or more cell types are on one side of the porous membrane and in addition one or more layers of one or more cell types are on the contralateral side of the porous membrane. One example that serves to illustrate this principle is the model of the blood brain barrier that includes a layer of vascular endothelial cells cultured together with a layer of central nervous system cells. In some cases it may be advantageous to culture both layers on one side of the porous membrane, for example on the side of the porous membrane that is contralateral to the culture medium. In these cases it may be advantageous to culture the endothelial cell layer adjacent to the porous membrane and the central nervous system cell layer adjacent to the endothelial cell layer. If molecules introduced to the culture medium were then detected in the central nervous system cell layer it could be inferred that they had crossed the endothelial cell layer, provided that the format of the cultures did not permit the molecules to by-pass the endothelial cell layer by movement directly across the porous membrane to the central nervous system cell layer. Similarly culture of the endothelial cell layer on one side of the porous membrane and culture of the central nervous system cell layer on the contralateral side of the porous membrane would ensure that molecules introduced to the medium adjacent to the endothelial cell layer had crossed the endothelial cell layer in order to reach the central nervous system cell layer, provided that the format of the cultures did not permit the molecules to by-pass the endothelial cell layer by movement directly across the porous membrane to the central nervous system cell layer. In this latter case, however, direct contact between the endothelial cells and the central nervous system cells would be prevented by the porous membrane. To ensure that the format of the cultures does not permit molecules to by-pass one layer to reach another layer distal to the porous membrane, the present invention provides for devices which enable layers of the same size to be assembled. These devices include conduits to hold the cell suspension prior to and during compaction, for example compaction by centrifugation. Cell types can be assembled in layers by the sequential introduction of different cell types to the conduit and the sequential compaction of layers of each cell type. The shape of the conduit can be designed to ensure that a subsequent layer of cells has a diameter no larger than a prior layer of cells.

Alternatively, cells from different organs may be compacted separately prior to culture and placed at different locations on the surface for culture such that they interact during growth. For example, the compacted cells from one organ may be placed several millimeters away from the compacted cells from another organ on the surface. In this situation, the compacted cells from the two organs are preferably separated by a space of less than 5 mm, more preferably less than 3 mm. The method of the invention may also involve co-culturing more than one group of compacted cells from the same organ at different locations on a surface to provide a model for the interaction of these cells. These compacted cells may be from different regions of one organ, or may be from the same region of one organ. Example 1 describes the preparation of two groups of compacted cells from the cortical region of the brain that were placed on different regions of a porous membrane separated by 3 mm to create a model of the corpus callosum when the two groups of cells interacted.

In some cases it is advantageous to place different cultures of compacted cells on different regions of a porous membrane by transferring the pellet produced by centrifugation of each type of dissociated cells to a different region of the surface following centrifugation. In other cases it is advantageous for the compaction of the different cell types by centrifugation and transfer of the compacted cells of each cell type to the surface to be carried out simultaneously. In these latter cases it is advantageous to provide a separate conduit to hold each cell suspension in the correct orientation with respect to the surface for compaction by centrifugation. Several such conduits can be provided to place each individual culture on a different region of the surface. Each such individual culture can contain one cell type or several cell types. If such individual cultures contain more than one cell type, these cell types can be mixed at random or can be assembled in layers by the sequential introduction of different cell types to the conduit and sequential compaction of each cell type.

The cells used in the methods of the first aspect of the invention may be derived from healthy organs or from diseased organs. As described in more detail below, the ability of the methods of the first aspect of the invention to generate organotypic cultures quickly and easily means that the methods will have extensive applications in the production of organotypic cultures for the study of disease links and for drug screening. Comparison of organotypic cultures obtained by the methods of the invention from healthy organs and diseased organs will further current knowledge of disease states and allow the identification of biomarkers and drug targets which are indicative of disease states.

The cells used in the methods of the invention may be genetically altered. For example, the cells may be genetically altered to modulate expression of a drug target or a biomarker. A biomarker is a molecular marker, the presence of which at a certain level or in a certain molecular form indicates the presence of a diseased state. A drug target is a molecular species that can be modulated to affect a disease process, i.e. a molecule through which a drug acts. Changing the nature or level of function of the drug target must have a positive impact on disease outcome, and the target should be of a molecular type that is amenable to modulation. In many cases, information about drug targets is obtained from genetic and other biological studies, and classes of compounds that are known to interact with those targets are available. It is often desirable to modulate the levels of these biomarkers and drug targets in biological systems, and to study the biological consequences.

Alternatively, the cells may be genetically altered to express a visual marker, such as a fluorescent marker, that allows the cells to be tracked visually.

Technologies to express cloned genes and to ablate the expression of cloned or endogenous genes are known in the art. These technologies may be used to increase or decrease expression of a marker, such as a drug target or biomarker, in the cells used in the methods of the invention. For example, the expression of a drug target may be modulated in selected dissociated cells before the cells are compacted and the organotypic culture is prepared. This approach is much more efficient than attempting to alter expression of a drug target in the final organotypic culture because single dissociated cells can be manipulated much more easily.

Techniques to increase expression of a cloned or endogenous gene are based on the introduction of heterologous DNA in a form which recruits the cellular expression system, and many different approaches are well known to those skilled in the art. In some cases naked DNA may be used with a lipophilic transfection reagent, the DNA including a strong promoter co-linear with the gene to be expressed and a replication origin that enables cytoplasmic replication of the introduced DNA. In other cases a viral vector may be used to increase the efficiency of DNA introduction. Similarly, means to ablate gene expression that are well known to those skilled in the art including antisense DNA oligonucleotides, peptide nucleic acid and double-stranded RNA interference. In some cases, naked nucleic acid may be used. In other cases, especially for the use of small interfering RNA, expression vectors may be used to express the molecule in a self-assembling hairpin form. It has also been shown that proteins can be introduced directly into cells provided that they are attached to an entity that encourages transport from the exterior to the interior of the cell. The Tat protein of human immunodeficiency virus (HIV) is one such entity, and proteins to be transferred may be produced as fusion proteins with HIV-Tat and introduced into cells (Becker-Hapak M. et al, 2001).

It will also be clear to those skilled in the art that, instead of transforming or transfecting the cells as described above, the cells used in the method of the invention may be from a transgenic animal. For example, the cells may be from a transgenic animal expressing a visual marker, such as a fluorescent marker, of from a transgenic animal in which expression of a particular drug target or biomarker has been increased or decreased.

Preferably, the surface on which the compacted cells are cultured in the method of the invention is optically transparent to allow the use of microscopy with an objective lens to view the cells from either side of the surface. Where the surface on which the compacted cells are cultured is a porous membrane, it is preferably a hydrophilic polytetrafluoroethylene (PTFE, also known under the DuPont trade name Teflon®) membrane which is optically transparent. Examples of alternative membranes for use in the methods of the invention may be made of polycarbonate, PET (polyethylene terephthalate), or Anopore™ (inorganic aluminium oxide, a trademark of Whatman Corp).

The compacted cells are cultured in the presence of a medium that provides the nutrients necessary for organotypic growth. Preferably, the medium is a liquid medium. Examples of suitable liquid media are described, for example, in Stoppini L. et al (1991) and Muller et al (2001).

According to a further embodiment of the first aspect of the invention, the method of the invention may further comprise the step of cryopreserving the resulting organotypic culture. Cryopreservation allows accumulation and storage of cultures to be used for screening purposes. Typically the cryopreservation is accomplished by freezing at the temperature of liquid nitrogen.

Unlike the prior art methods that require artificial matrices composed of specialised materials, the method of the invention does not require any specialised materials and can therefore be carried out on a large scale, allowing the preparation of multiple organotypic cultures in parallel. The invention therefore provides a high-throughput method for the preparation of a collection of organotypic cultures, said method comprising preparing multiple organotypic cultures according to the method of the first aspect of the invention in parallel. Preferably, the high-throughput method of the invention is carried out using mass-produced pre-fabricated culture devices and robotic dispensing.

Preferably, the method of the first aspect of the invention is carried out in a device which allows multiple parallel cultures per device, preferably 2, 4, 8, 16, 24, 96, 384, 1536 or more parallel cultures per device.

According to a second aspect of the invention, there is provided a device for carrying out the method of the first aspect of the invention. Preferably, the device is small enough to allow thousands of cultures, preferably tens of thousands of organotypic cultures, to be prepared and maintained simultaneously, by culturing devices in parallel. Each culture may be maintained on a separate surface or on a separate section of a large surface and nourished separately. Preferably, the culture device further incorporates electrodes for the measurement of elecrophysiological response in the organotypic cultures produced. A suitable device is described in European patent EP1133691.

As discussed above, where the method of the first aspect of the invention involves the culture of compacted cells on a porous membrane, the method preferably comprises supplying the contralateral surface of the membrane with nutrients, preferably in the form of liquid medium. Preferably, the liquid medium is retained at the membrane surface by capillarity, resulting in further compaction of cells on the membrane. The invention also therefore provides a device adapted to carry out this preferred method of the first aspect of the invention. According to preferred embodiment of the second aspect of the invention, there is therefore provided a device for carrying out the method of the first aspect of the invention, said device comprising:

a conduit having one open end and one end closed by a porous membrane fused across it; and a frame holding the conduit in a substantially vertical orientation;

wherein the conduit is adapted to permit retention by capillarity of a sufficient volume of liquid in the culture medium in the conduit to contact the surface of the porous membrane and thus supply nutrients to cells that may be grown on the porous membrane.

The use of the force of capillarity to maintain the culture medium in the conduit enables the removal and replacement of the culture medium by a pipetting step in either the upright or inverted orientations. When supplying the medium, the pipette tip should be positioned as closely as practicable to the surface of the membrane.

Preferably, the conduit is adapted such that it retains a sufficient volume of liquid culture medium by capillarity to maintain contact between the surface of the porous membrane in the conduit and the culture medium when the device is in either the upright or inverted position.

By upright position is meant that the frame holds the conduit substantially vertically with the end sealed by the porous membrane positioned uppermost so that, when the device is in use, the organotypic culture is grown on the upper surface of the membrane. By inverted position is meant that the frame holds the conduit substantially vertically with the open end positioned uppermost and the end closed by the porous membrane lowermost so that, when the device is in use, the organotypic culture in the lower surface of the membrane. In contrast to the devices that are available in the art, the device of the invention thus allows incubation of the organotypic culture and change of the medium for the organotypic culture with the device in either the upright or inverted position. This flexibility in orientation of the culture and the device means that either microscopes with their objective lenses facing upwards or microscopes with their objective lenses facing downwards can be used interchangeably for studying the culture, and that liquid handling devices can be used in either orientation to add or remove the medium.

Preferably, the conduit is a cylinder. The conduit may also be of rectangular or asymmetrical cross-section. The exact dimensions and composition of the conduit are selected such that, during organotypic culture, it retains a sufficient volume of liquid culture medium by capillarity to maintain contact between the surface of the porous membrane in the conduit and the culture medium, preferably irrespective of whether the device is in the upright or inverted position. The volume of liquid retained should be sufficient such that in use, adequate nutrients are supplied to the organotypic culture without requiring the medium to be changed at unreasonably short intervals.

Capillarity is dependent on several parameters. The force of capillarity is an inverse function of the diameter of a cylindrical vessel or the width or breadth of a conduit of rectangular section. The force of capillarity on an aqueous solution also depends on the surface tension of the solution being held by that force which can be weakened by the presence in solution of surfactants such as detergents. Capillarity is affected by the degree of attraction between the molecules of the liquid and the molecules of the surface. In the case of an aqueous liquid, capillarity is affected by the degree of hydrophilicity of the surface of the conduit. A further factor affecting the retention of liquid culture medium in a conduit is the volume of the culture medium. These factors therefore need to be taken into account to ensure that the device of the invention can retain a volume of liquid media in contact with the surface of the porous membrane by capillarity.

In the device, two different capillary forces act to retain the liquid medium in the conduit in contact with the porous membrane. The force of capillarity exerted by attraction between the liquid medium and the tube is one force. The other force is exerted by attraction between the liquid medium and the walls in the pores of the membrane. If sufficiently strong, the former will counteract gravity to keep the liquid in the conduit irrespective of whether it is upright or inverted, and the latter will keep the liquid in contact with the membrane. At a certain threshold, the force of gravity on the culture medium will exceed the force of capillarity and culture medium not restrained by an additional force will fall from the conduit.

Where the conduit is a cylinder, the mass of the liquid contained in the cylinder and thus the gravitational force acting to remove the liquid from the cylinder is directly proportional to the square of the radius of the cylinder, whereas the capillary force acting to retain the liquid in the cylinder is inversely proportional to the radius. Thus for a given liquid and cylinder length there is a maximum radius above which the liquid in a cylinder of a given surface composition will not be retained against the force of gravity, but there is no minimum radius below which liquid will not be retained against the force of gravity.

Preferably, the conduit is a cylinder having a radius of 0.5 cm or less, preferably 0.3 cm, 0.25 cm, 0.2 cm, 0.15 cm or less. Preferably, the cylinder has a radius of approximately 0.3 cm, 0.15 cm or 0.075 cm. It has been found that cylindrical conduits having a radius of 0.5 cm or less are adapted to maintain a 1 cm column of a standard liquid culture medium, such as Dulbecco's Minimum Essential Medium, in contact with the surface of the porous membrane in the conduit, irrespective of whether the device is in an upright or inverted position.

Preferably, the conduit, preferably a cylinder, is about 1 cm in length, to allow it to retain a 1 cm column of liquid. Preferably, the conduit is slight greater than 1 cm in length, preferably approximately 1.1 cm or 1.2 cm in length.

Preferably, the conduit is made of a hydrophilic material, preferably a hydrophilic polymer, to increase force of capillarity exerted on the liquid medium when it is in the conduit. Hydrophilic polymers will be known to the person skilled in the art. The hydrophilicity of polymers from which the conduit is made may be increased further, for example by inclusion of polyethylene glycol groups.

The device of the second aspect of the invention is not limited to cylinders with a radius of less than 0.5 cm as it will be well within the skilled person's ability to determine the dimensions of other conduits which may be used in the device. Specifically, the skilled person will be able to calculate the forces of capillarity and gravity exerted on a given volume of liquid culture medium in conduits of different dimensions and thus determine what dimension of conduit should be employed in the device to ensure that the forces of capillarity exceed the forces of gravity such that the liquid is retained in the conduit. Furthermore, constrictions, platforms or other obstructions may be included in the conduit to increase resistance to the force of gravity acting to remove the medium from the conduit.

According to the Laplace-kelvin equation, $$\text{force of capillarity} = \text{surface tension}/(R1-R2),$$

where R1=the radius of a tube or pore (in this case a conduit) in cm and R2=the thickness of the meniscus layer in contact with the wall of the tube or pore.

1 dyne is the force required to accelerate 1 gram at 1 cm $sec^{-2}$. The surface tension of an aqueous medium is about 73 dyne $cm^{-2}$ unless surfactants such as detergents are included. It is not common practice to include detergents in culture media but proteins can also affect surface tension and proteins are commonly included in media particularly in the form of serum. Generally, the surface tension of a liquid culture medium is at least 50 dyne $cm^{-2}$. The total force of gravity acting on a given volume of liquid culture medium is 98× (volume in $cm^3$) dyne. The thickness of the meniscus layer (R2) generally need not be taken into consideration when calculating capillarity for the purpose of the present invention. When R2 is small, it has a negligible effect on capillarity and as R2 approaches R1, the capillarity force becomes greater. As it is only necessary to determine whether the minimum capillary force requirements are met for a given conduit and aqueous medium for the purpose of the present invention, measurement of R2 is not necessary. It is, however, of course possible to measure R2 if it is desired to calculate the force of capillarity more precisely.

For a cylinder of length 1 cm and a radius of 0.5 cm, a total capillary force of at least 77 dyne would therefore be required to counteract the force of gravity and maintain a 1 cm column of liquid with surface tension 50 dyne $cm^{-2}$ in the cylinder by capillarity when inverted. If the hydrophilicity of the cylinder surface is sufficiently high, the force of capillarity can apply a force of greater. 100 dyne to such a column of liquid.

For a cylinder of length 1 cm and a radius of 0.3 cm, a total capillary force of at least 28 dyne would be required to counteract the force of gravity and maintain a 1 cm column of liquid with surface tension 50 dyne $cm^{-2}$ in the cylinder when inverted. If the hydrophilicity of the cylinder surface is sufficiently high, the force of capillarity can apply a force of greater than 170 dyne to such a column of liquid.

These forces of capillarity are sufficient to retain such a column of liquid when inverted provided that the device is not moved or vibrated, because accelerations caused by movement or vibration change the momentum of the column of liquid and can overcome the restraining force. Preferably, the dimensions of the conduit are such that no reasonable changes in momentum such as may be caused by normal manual or robotic manipulations result in the loss of liquid from the conduit.

Preferably, the dimensions of the conduit are selected such that the capillary force acting to retain a given volume of liquid medium at the surface of the porous membrane is at least 6 times the gravitational force acting to release the medium. A capillary force of 6 times the gravitational force has been found to be adequate to ensure retention of liquid media in the conduit of the device under normal handling, even when the medium contains protein components such as those in serum that diminish the surface tension of the medium.

Preferably, the porous membrane is fused across one end of the conduit by gluing or by heat-sealing or by ultra-sonic sealing. The porous membrane applies a capillary force to the liquid in the conduit according to the Laplace-Kelvin equation (see above), depending on the radius and surface composition of the pores in the membrane. This capillary force exerted by the membrane should be sufficient to wet the membrane and keep the liquid in contact with the membrane. Preferably, the porous membrane in the device of the invention comprises pores with a size of ~0.4 µm. Membranes suitable for use in the device of the invention include but are not limited to the hydrophilic polytetrafluoroethylene (PTFE, also known under the DuPont trade name Teflon®) membrane produced by Millipore Corporation which is optically transparent, membranes made of polycarbonate, PET (polyethylene terephthalate), or Anopore™ (inorganic aluminium oxide, a trademark of Whatman Corp).

Preferably, the porous membrane is optically transparent. This feature enables the test cultures to be accessible at all times to microscopic examination and sampling for biochemical assays. Preferably, the porous membrane produces low background fluorescence at the wavelengths used for excitation, usually in the range of 400-750 nm. Preferably, the porous membrane is composed of hydrophilic polytetrafluoroethylene (PTFE) membrane.

Preferably, the frame holds the conduit in a vertical orientation such that neither the end of the conduit closed by the membrane nor the open end of the conduit is in contact with any surface. Preferably, the device further comprises a sealing ring which ensures that the frame is held firmly in contact with the conduit. Preferably, the device comprises two such sealing rings. The device may further comprise additional means to ensure that the frame is held firmly in contact with the conduit so that the conduit is not released when it is inverted. Such additional means may comprise, for example, friction means such as springs between the frame and the conduit.

Preferably, the device further comprises a chamber enclosing the open end of the conduit. The chamber may form part of the frame holding the conduit in a vertical orientation. When the device is in use, the chamber contains an atmosphere of suitable gaseous composition that contacts the medium in the conduit to maintain optimum acidity and oxygen levels in the medium. The chamber is preferably sealed to ensure that the liquid medium is not exposed to the external atmosphere during use. The chamber may further comprise a gas inlet and a gas outlet to allow control of the atmospheric conditions in the chamber.

Preferably the device further comprises one or more conduits preferably removable conduits to contain the cells prior to and during compaction, such conduits or removable conduits placed on the contralateral side of the membrane to the conduit that contains the culture medium. The use of more than one conduit to contain the cells prior to and during compaction enables more than one culture to be established on different sites within the region of the membrane in contact with each conduit of culture medium. If the conduits that contain the cells are not removable, they may be sealed permanently to the porous membrane by gluing or by heat-sealing or by ultra-sonic sealing. If the conduits that contain the cells are removable they are sealed to the porous membrane non-permanently. Examples of non-permanent seals include shaped edges that focus pressure and silicone and other compressible substances which may comprise all of the conduit or the sealing edge of the conduit. It will be appreciated by those familiar with centrifugation that the application of a gravitational field to a device including a conduit proximal to the porous membrane with respect to the axis of rotation of the centrifuge rotor will press the sealing edge of the conduit against the porous membrane. In the case of a removable conduit this enhances the sealing properties of the sealing edge. It will also be appreciated by those skilled in the art of design of devices for use in gravitational fields that load-bearing surfaces must be supported by structures of adequate strength to avoid failure. For example, the porous membrane of the invention does not have adequate strength to support a conduit in even a weak gravitational field without damage to the porous membrane. Therefore steps have been taken to ensure that the conduits of the invention are supported by structures of adequate strength within the frame of the device. If a compressible seal is used between a conduit and a porous membrane, the degree of compression under the influence of a gravitational field is in all cases limited by contact of the conduit with a structure of adequate strength within the frame of the device. These considerations are obvious to those skilled in the art of design of devices for use in gravitational fields.

Preferably, the sealed chamber further comprises an opening to allow the culture medium to be changed. Preferably the opening is designed to minimise exposure of the culture medium to the atmosphere when the medium is changed. The opening may be sealed by a septum or valve that it is normally sealed but may be penetrated by a pipette tip to withdraw the medium and introduce new medium. The septum may be made of rubber or neoprene. The opening may also be used to introduce specific components to the existing medium, such as growth factors or antibiotics or toxins, rather than to change the medium completely. Preferably, the pipetting step is conducted without subjecting the culture to a significant change in hydrostatic pressure.

It will be apparent to those skilled in the art of manual and robotic pipette construction that to withdraw liquid from the conduit, a negative pressure must be applied that is greater than the pressure retaining the liquid in the conduit. It will be important to avoid damage by the pipette tip to the porous membrane, and for this reason the pipette tip will not be advanced into contact with the said membrane. It may not therefore be possible to remove all the liquid medium from a conduit with a single pipetting step Liquid may be retained in the conduit in the region of the conduit between the point of furthest travel by the pipette tip and the membrane. Such retention of liquid in the conduit by capillary force is most likely to apply with very small cylinder radius, although it will also depend upon the precise properties of the pipette tip and the liquid. If retention of liquid does occur, it will not, in most cases, affect the health of the culture.

In some circumstances, however, for example if exposure of the culture to a toxic substance is being tested, retention of liquid could potentially influence experimental data. In this case the pipetting steps of liquid removal and replacement with fresh liquid may be repeated as many times as necessary to remove the toxic substance by dilution. For example, if the cylinder is 1 cm long and the pipette tip can be safely advanced to within 0.1 cm of the membrane, then at most 10% of the volume may be retained in the cylinder. The addition of fresh liquid to the full 1 cm length would dilute the toxin to 10% of its original concentration. Repetition of this process would dilute the toxin to 1% of its original concentration. The time programming of pipetting steps would take into account the need to allow equilibration of the toxin to maximise the efficiency of removal by dilution.

Preferably, the device further comprises a lid that covers the surface of the porous membrane outside the conduit. The lid covers the surface of the porous membrane on which the culture is located when the device is in use. If a conduit is used to contain the cells prior to and during compaction and the said conduit is fixed permanently, the lid covers the said conduit. If a conduit is used to contain the cells prior to and during compaction and the said conduit is not fixed permanently, the said conduit may be removed prior to the fitting of the lid. Where the device comprises a lid, the chamber and the frame preferably comprise additional ports to allow gas flow between the chamber and the space above the membrane enclosed by the lid, allowing the atmosphere surrounding the culture to be controlled and to be kept sterile over periods of several weeks or more.

The device of the second aspect of the invention is preferably adapted for use in high-throughput methods that involve preparing and maintaining multiple organotypic cultures simultaneously. According to a second embodiment of this aspect of the invention, there is therefore provided a device for high-throughput organotypic culture comprising multiple devices according to the first aspect of the invention. Preferably, the device for high-throughput organotypic culture comprises 96, 384, 1536 or more devices according to the second aspect of the invention.

The high throughput device may thus contain thousands of conduits, each of which can be supplied independently with culture medium and for which the culture medium can be changed independently. Preferably, the medium change is carried out by a multichannel pipette or robot as described above.

Preferably, the high-throughput device comprises a single lid covering all of the individual conduits within the device.

Preferably, the chambers enclosing the open ends of each conduit in the high-throughput device are connected by an opening, allowing gas flow between the chambers so that gas flow to all of the chambers within the device may be controlled by a single gas flow inlet and outlet in the high-throughput device.

The multiple devices in the high-throughput device may be fabricated as a single unit. Alternatively, the high-throughput device may be supplied as individual devices each containing a single conduit that can be assembled into a high-throughput device containing the desired number of conduits by the user. The high-throughput device may also be supplied as strips of individual devices, for example, in batches of 2, 4, 8, or 12, that can be assembled into a high-throughput device containing the desired number of conduits, optionally by the user. High-throughput devices comprising strips containing a set number of wells are known in the art for cell culture, although not for organotypic culture. A multiwell device of this type has been described by Dynatech in Thorne A. (1979) in U.S. Pat. No. 4,154,795.

Preferably, for high-throughput devices, the overall size of the device and the position of the individual conduits within the device should match the size of a standard microtitre plate to enable the device to be use with robotics designed for standard microtitre plates. For example, in a high-throughput device comprising 96 devices, the devices are preferably arranged in an array of 8 by 12 devices, resembling a standard 96 well microtitre plate. The conduits in the 96 devices making up the high-throughput device are preferably cylinders. Preferably, each cylinder has a radius of approximately 0.3 cm which is the radius of a well in a standard 96 well microtitre plate. The capillary and gravitational forces acting in such a cylinder have been described above.

In a high throughput device comprising 384 devices, the conduit in each device is preferably a cylinder and the cylinder radius is preferably approximately 0.15 cm, the radius of a well in a standard 384 well microtitre plate. The weight of the liquid in this cylinder of the same 1 cm length is only 25% of the corresponding weight with a cylinder diameter of 0.3 cm, but the capillary force is doubled compared to the aforesaid larger cylinder. In a high throughput device comprising 1536 devices, the conduit in each device is preferably a cylinder and the cylinder radius is cylinders is preferably approximately 0.075 cm, the radius of a well in a standard 1536 microtitre plate. In this case the weight of liquid in the cylinder of the same 1 cm length is only 6.25% of the corresponding weight with a cylinder diameter of 0.3 cm, but the capillary force is four-fold higher. Thus, devices of 96, 384 or 1536 cylinders made according to the invention to the overall size of a standard microtitre plate all retain liquid in the cylinders in the inverted position.

According to a third aspect of the invention, there is provided an organotypic culture or a collection of organotypic cultures obtained by the methods of the first aspect of the invention. Although the organotypic cultures produced from compacted cells by the methods of the first aspect of the invention retain the same functional characteristics as an organotypic organ slice culture, they differ from organotypic organ slice cultures in terms of their anatomical structure.

An organotypic organ slice culture retains the anatomical features of the source organ in so far as those features occur in the region of the organ which is cut to create the slice. For example, a transverse slice made from the hippocampal region of the brain retains the typical cellular arrangements that characterise the hippocampus, for example the spatial arrangement of the CA1, CA2 and CA3 regions. The organotypic cultures made according to the methods of the first aspect of the invention differ from organotypic cultures made from slices because the anatomical features are lost by dissociation of the cells in the organ or by cutting the organ into multiple explants or microexplants.

Surprisingly, despite this loss of anatomical features, organotypic cultures made according to the methods of the first aspect invention have organotypic features, i.e. they retain the functional characteristics of organs. For example, it can be seen in FIG. 1 that a culture made according to the method of the first aspect of the invention from compacted dissociated cells from cerebral cortex has no anatomical differentiation. However, the intercellular connections that are created within the culture during the period of culture occur between cells that would normally form connections in vivo. The reason for the accuracy and appropriateness of these connections appears to be the production by each cell of the chemical signals that it would produce in vivo, and the appropriate responses of other cells to those signals.

The response to the signals will depend on the normal function of the cells. In some cases, the cells that respond to such signals may respond with the extension of cellular processes such as the axonal processes of neurons. In other cases, the cells that respond may respond with cellular processes that lead to cellular movement through the culture either towards or away from the cell or cells producing the signal. Alternatively, the cells that respond may respond with cell division or cell division that they might otherwise undergo may be inhibited. The cells that respond may also respond by producing other signals to which cells respond that do not respond directly to the signals produced by the first cell. In this way, various changes in cell number, function and distribution may occur within the culture during the period of culture, and these changes result in organotypic behaviour of the culture.

There are numerous applications for the organotypic cultures of the third aspect of the invention obtained by the methods of the first aspect of the invention, as will be apparent to the skilled reader. For examples, the organotypic cultures may be used to study cellular functions and components, and the outcomes of intercellular communication, in a given healthy organ. These functions and outcomes are commonly altered in disease states and the organotypic cultures can be used to study diseased tissue as well as normal tissue and the impact of exogenous factors, including candidate drugs, on these disease states.

As described above, biomarkers are molecular markers which at a certain level or in a certain molecular form indicate the presence of a diseased state. A drug target is a molecular species that can be modulated to affect a disease process. One application of the organotypic cultures of the invention is in the identification of biomarkers and drug targets.

Screening of several molecular classes, such as proteins and lipids, in organotypic cultures that express a disease state or the corresponding non-diseased state may be used to identify biomarkers. Validated biomarkers are currently used both to identify carriers of a disease state and to monitor their progress towards normality that may be assisted by a therapeutic regime such as a drug. It is necessary to establish a statistically significant association between a candidate biomarker and a disease state to validate the biomarker for use in clinical trials. The organotypic cultures of the present invention are ideally suited to biomarker discovery and validation due to the fact that they replicate organ function and physiology and can be generated quickly and easily by the methods of the invention such they are applicable to high throughput assays. The organotypic cultures of the invention could thus be used much more rapidly and cheaply than whole animals currently used for the identification and validation of biomarkers.

According to a further aspect of the invention, there is therefore provided a method for the identification and validation of biomarkers and drug targets comprising screening the organotypic cultures of the third aspect of the invention. Assays for identifying biomarkers and drug targets include the use of transcriptional profiling, proteomics, mass spectrometry, gel electrophoresis, gas chromatography and other methods for molecular profiling known to those skilled in the art.

Surrogate markers are a sub-set of biomarkers that can be used to assess the presence or progression of a disease state, but that do not measure directly a clinical outcome of the disease. The organotypic cultures of the invention may be used to identify and validate surrogate markers in the same way as other biomarkers.

The organotypic cultures of the invention are not only useful in the identification of biomarkers and drug targets associated with disease states but are also useful in screening to identify drugs that alleviate these disease states. Organotypic cultures are particularly useful in the screening of candidate drugs because it is important for such screening that the target culture has biochemical and physiological properties that match as closely as possible those features of the target organ in vivo. It must be possible, however, for the organotypic culture to be used at high throughput to enable screening of sufficiently large numbers of drug candidates for a high probability of successful identification of lead drugs. Additional large-scale assays are often necessary to validate the inclusion of a lead drug in a preclinical and clinical drug development programme.

The methods of the first aspect of the invention may be used to generate many thousands of organotypic cultures simultaneously and are thus uniquely suited to high throughput applications involving multiple assays for each culture. In one embodiment, the methods for producing an organotypic culture according to the first aspect of the invention further comprises the step of screening using the resulting organotypic culture in a method of screening and pre-clinical validation of candidate drugs. As discussed above, one particularly useful aspect of the method of the invention is that it facilitates the high-throughput formation of organotypic cultures in which the cells have been genetically altered to modulate the expression of a biomarker or drug target. These modified organotypic cultures will also be useful in the screening of candidate drugs.

The field of toxicology is a further application area for the present invention that will benefit greatly by the enhanced flexibility and throughput provided by the methods of the invention. Organotypic response is crucially important in this field, because different tissues differ greatly in their response to toxins, with different clinical consequences. Different tissues can contain different enzymes systems, notably of the cytochrome P450 class, that metabolise different classes of exogenous compounds. The degree and type of metabolism of a compound can profoundly affect its toxicity. Large-scale screening of toxicity in a wide variety of tissues is so expensive at present that many chemicals in common use have never been tested adequately. Increasing awareness of potential toxicity has brought pressure to carry out such tests without the means to do so at acceptable cost.

The invention therefore also includes a method of assessing the toxicity of a chemical using the organotypic cultures of the present invention.

Various aspects and embodiments of the present invention will now be described in more detail by way of example. It will be appreciated that modification of detail may be made without departing from the scope of the invention.

FIGURES

Figure 1:
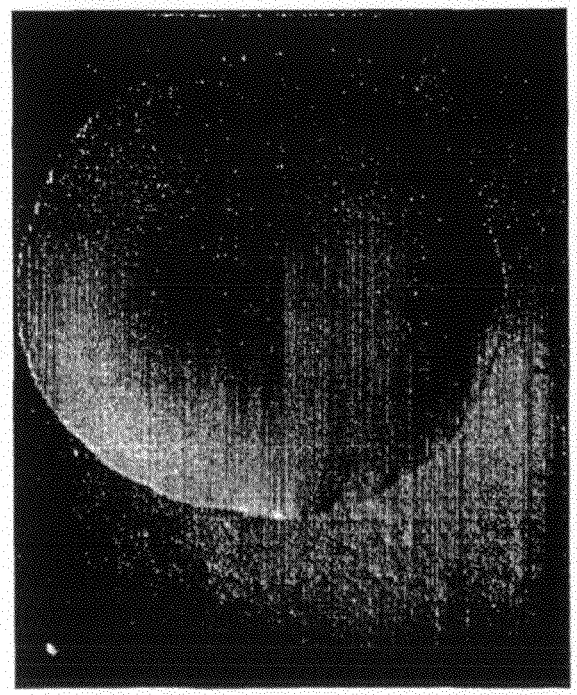

FIG. 1: Photomicrograph of a typical organotypic culture made according to the methods of the invention from dissociated mouse cortical cells.

Figure 2:
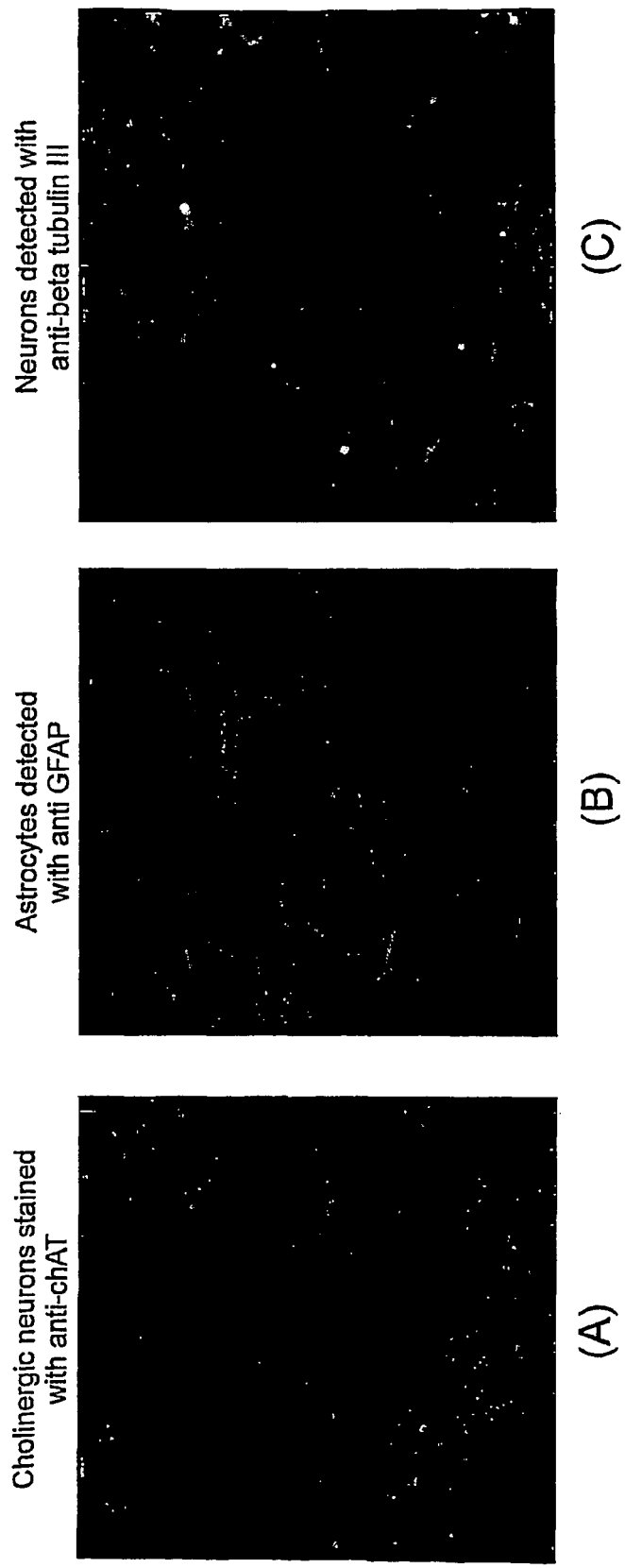

FIG. 2: Functioning neurons and glial cells after 5 weeks in an organotypic culture of mouse cortex.
  A. Cholinergic neurons stained with anti-ChAT.
  B. Astrocytes detected with anti-GFAP.
  C. Neurons detected with anti-beta tubulin III.

FIG. 3: Organotypic culture made according to the methods of the invention overlaid on a multi-electrode device for electrophysiological measurements.

Figure 4:
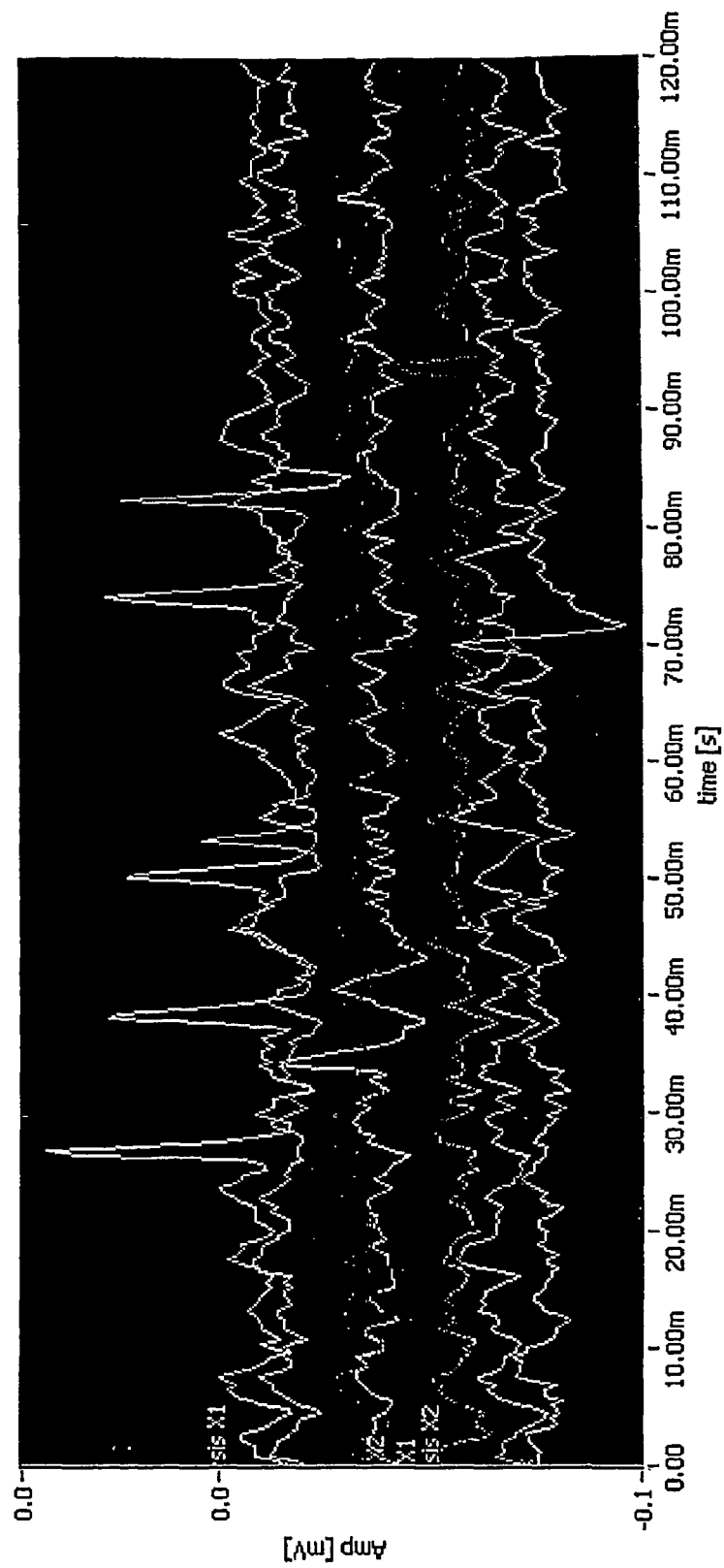

FIG. 4: Spontaneous field potential changes between 8 pairs of electrodes on the device of FIG. 3 upon which an organotypic culture is overlaid, the culture being made according to the methods of the invention from dissociated mouse cortical cells.

Figure 5:
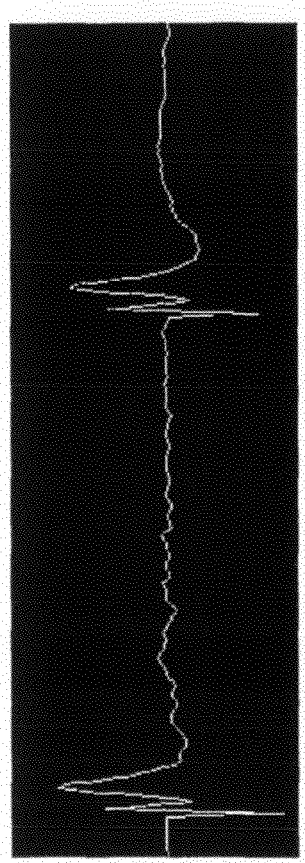

FIG. 5: Paired-pulse stimulations induce Evoked Field Potentials (EFP) from an organotypic culture made according to the methods of the invention from dissociated mouse cortical cells.

FIG. 6: Schematic diagram of co-culture of two organotypic cultures made according to the invention from dissociated cells from mouse cortex (denoted central nervous system (CNS)) placed to mimic the corpus callosum.

Figure 7B:
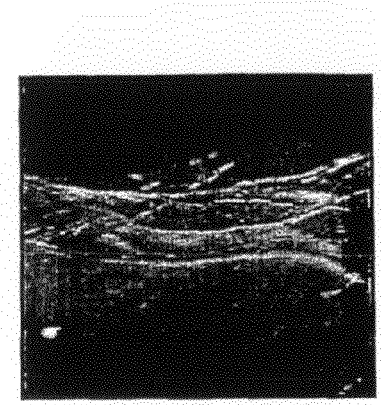
Figure 7A:
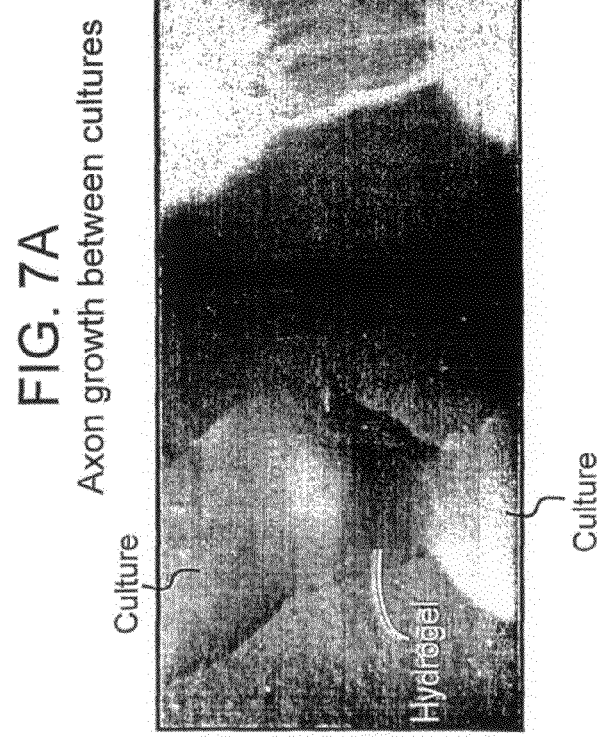

FIG. 7: Axon growth between two cultures of THY-1 GFP mouse cortex after 10 days of organotypic culture.
  A. low magnification views of both cultures and hydrogel bridge in bright field (left) and fluorescence (right) images.
  B. High magnification view of axons within the hydrogel.

Figure 8:
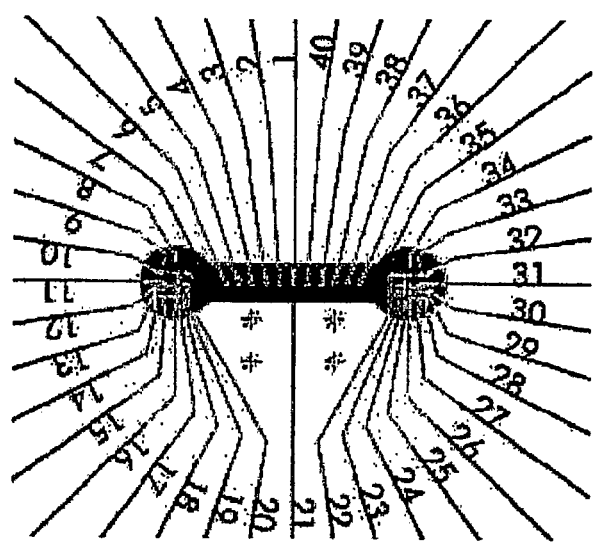

FIG. 8: Multi-electrode device for electrophysiological measurements integrated in a porous membrane.

FIG. 9: Electrophysiological responses of a culture made from frozen and thawed dissociated cells from mouse cortex.
  A. Paired-pulse evoked field potentials.
  B. Spontaneous activities.

Figure 10:
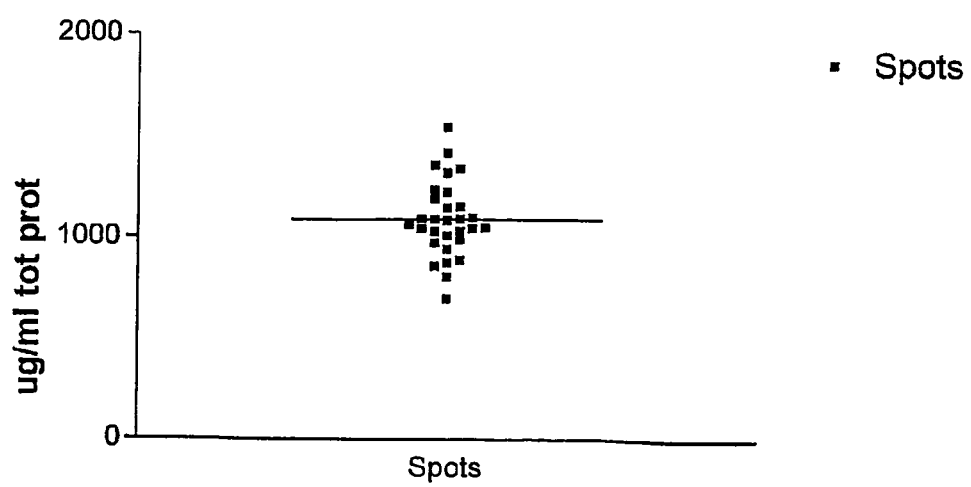

FIG. 10: Protein concentrations in replicate cultures of mouse cortex

Figure 11:
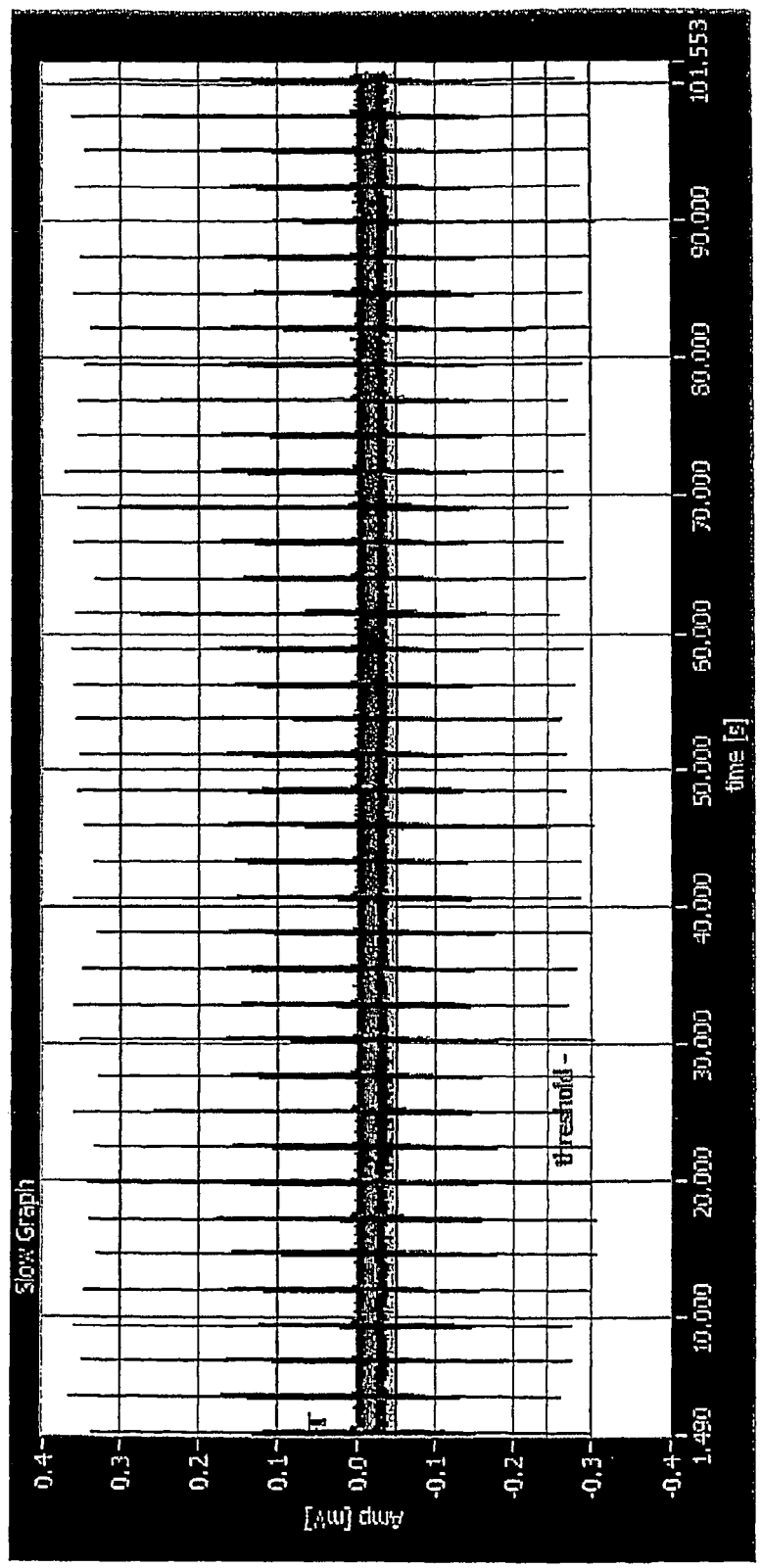

FIG. 11: Spontaneous field potential changes from 8 pairs of electrodes on the device of FIG. 8 underneath an organotypic culture made according to the invention from dissociated mouse cardiac muscle cells.

FIG. 12: Organotypic culture of mouse embryonic liver.
  A. bright-field
  B. stained with anti-smooth muscle alpha actin
  C. stained with Hoechst (nuclei)

FIG. 13: Organotypic culture of human foetal pancreas:
  A. bright-field
  B. stained with anti-insulin antibody
  C. stained with anti-SOX9 antibody
  D. stained with DAPI (nuclei)

FIG. 14: Organotypic culture of dissociated P0 mouse brain cells 24 hours after transduction with lentiviral vector expressing EGFP.

Figure 15:
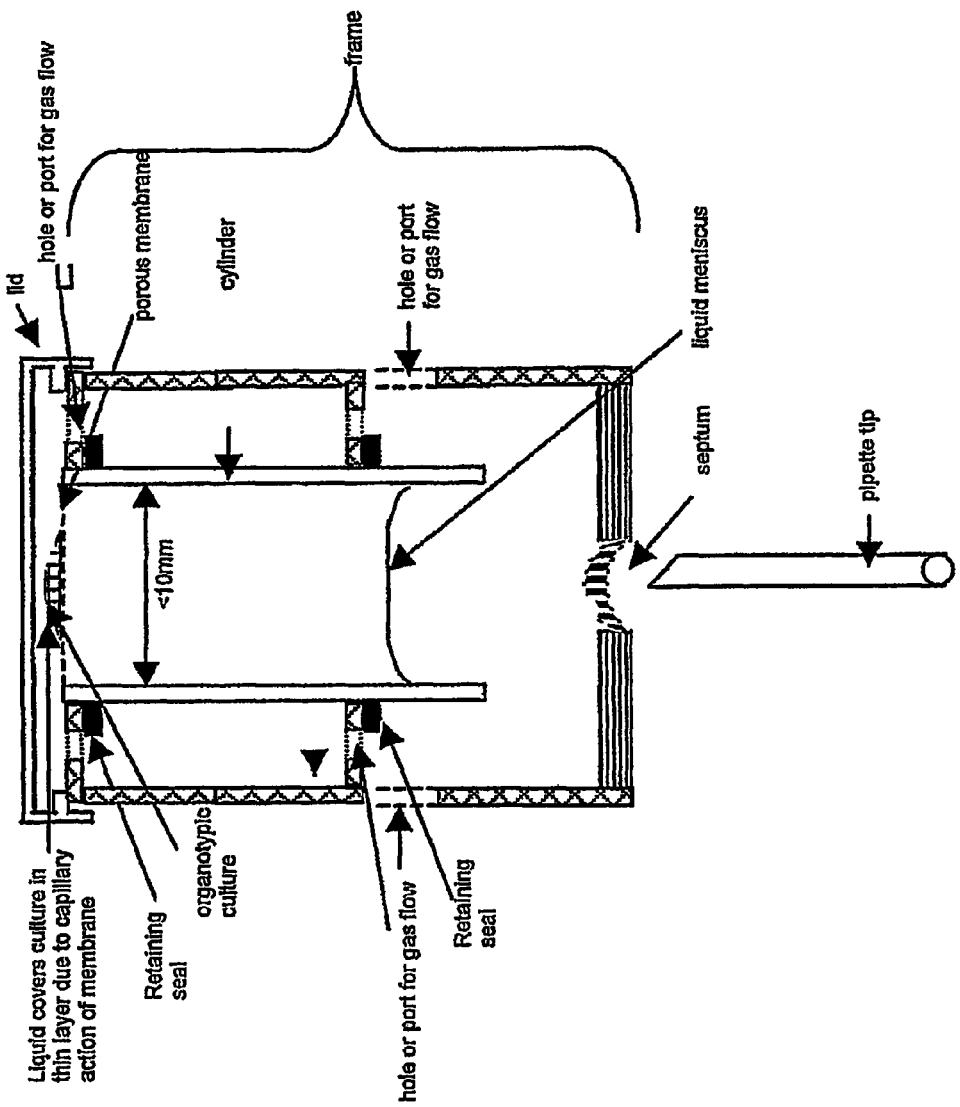

FIG. 15: Cross-section of a device for organotypic culture.

Figure 16:
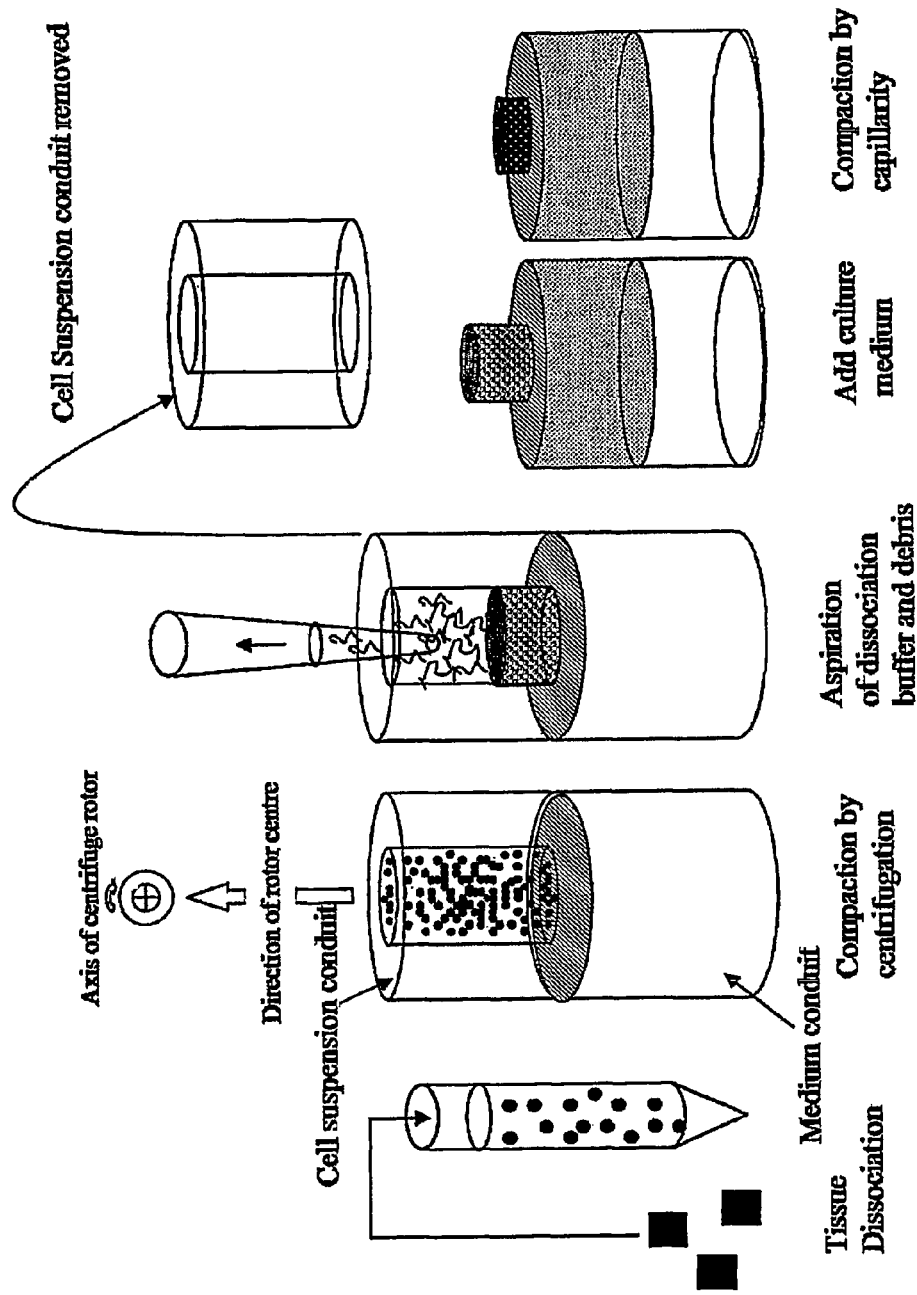

FIG. 16: Schematic description of the process of generating an organotypic culture in a device including a removable conduit for containing cells before and during compaction.

Figure 17:
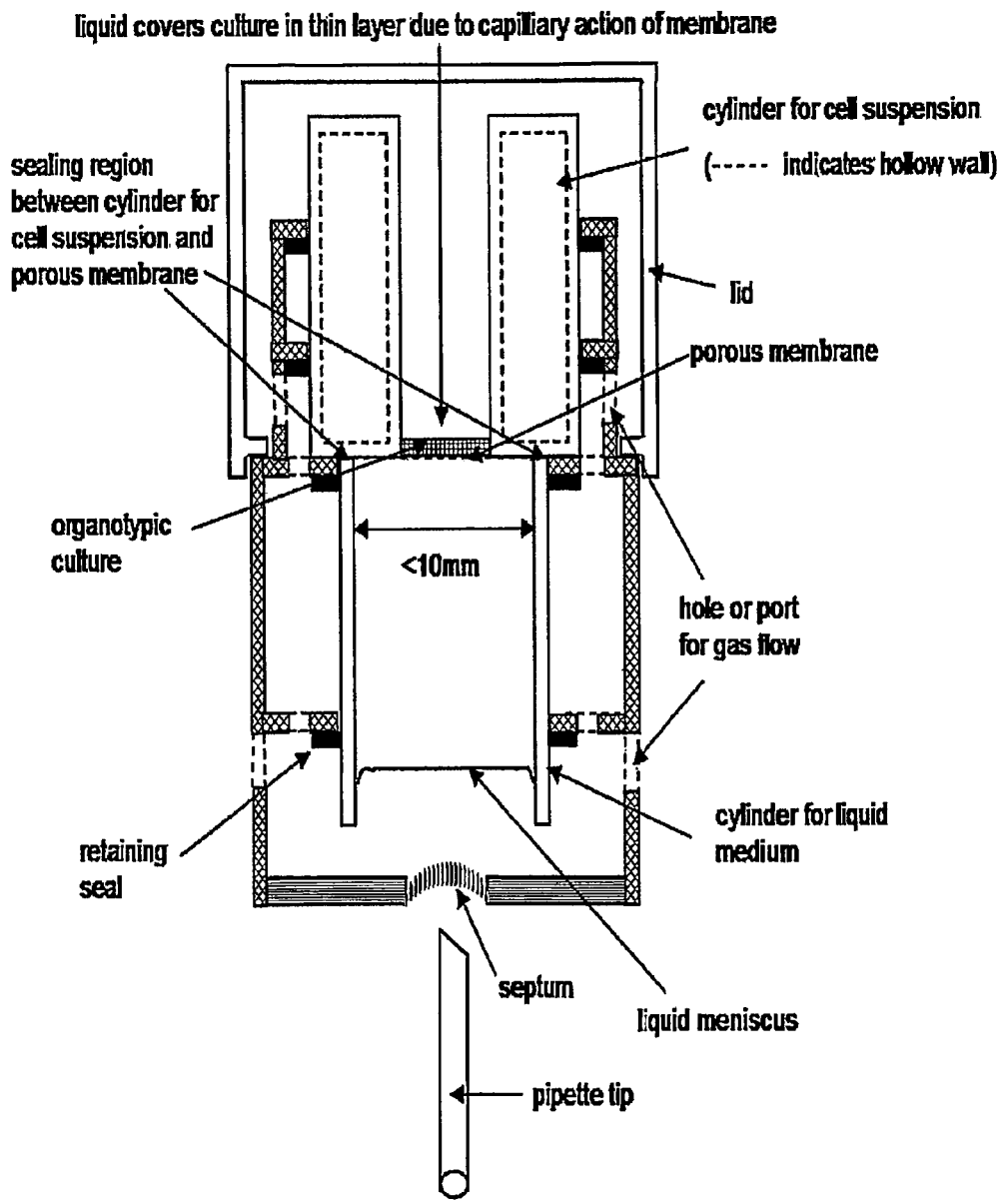

FIG. 17: Cross section of a device for organotypic culture including a conduit for containing cells before and during compaction.

Figure 18:
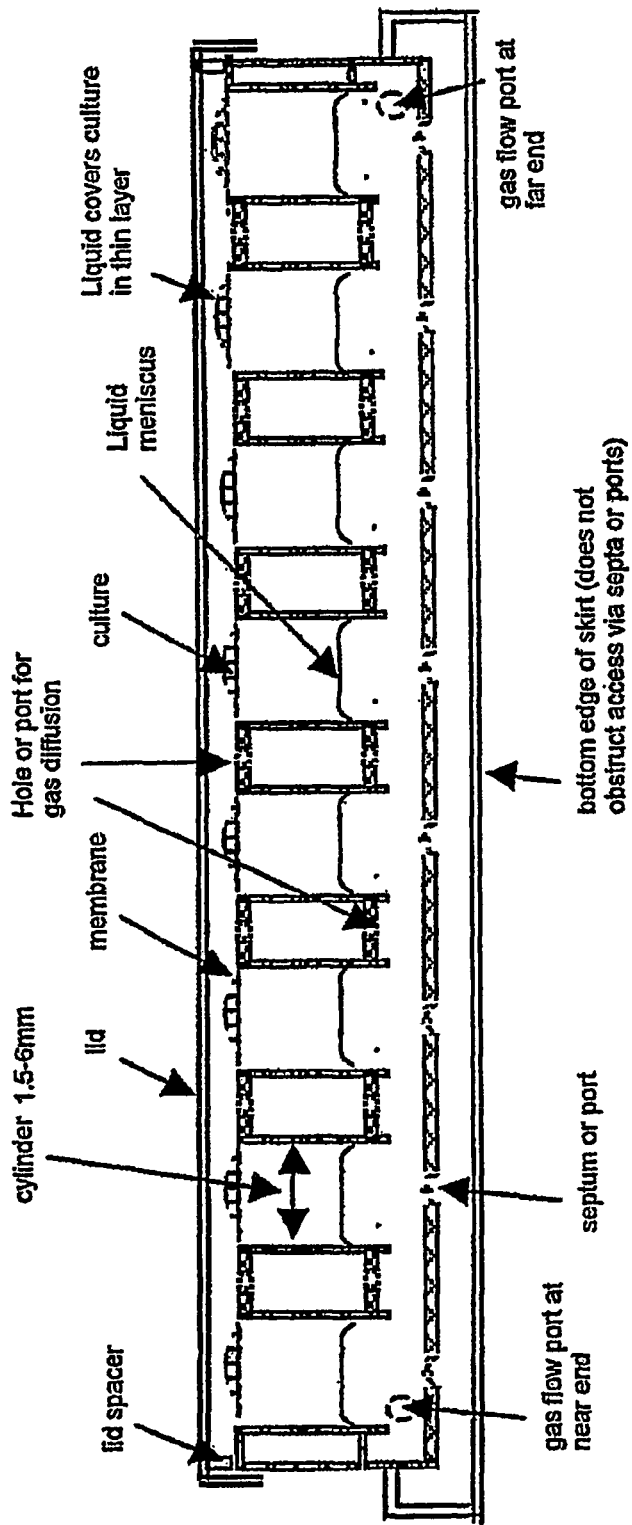

FIG. 18: Cross-section of a high-throughput device for organotypic culture.

Figure 19:
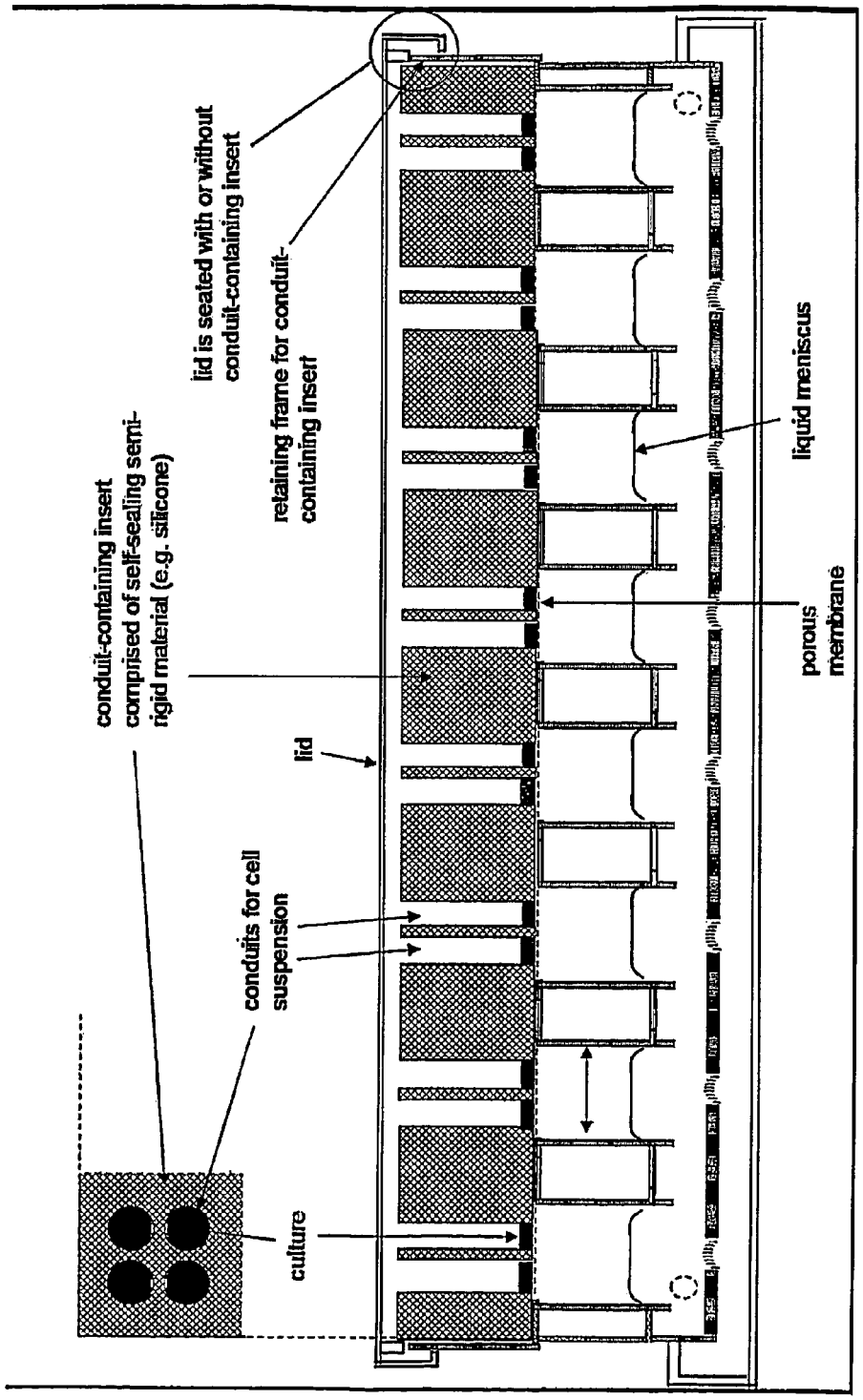

FIG. 19: High-throughput device and removable conduits for a high throughput device including 4 conduits per well for containing cells before and during compaction.

Figure 20:
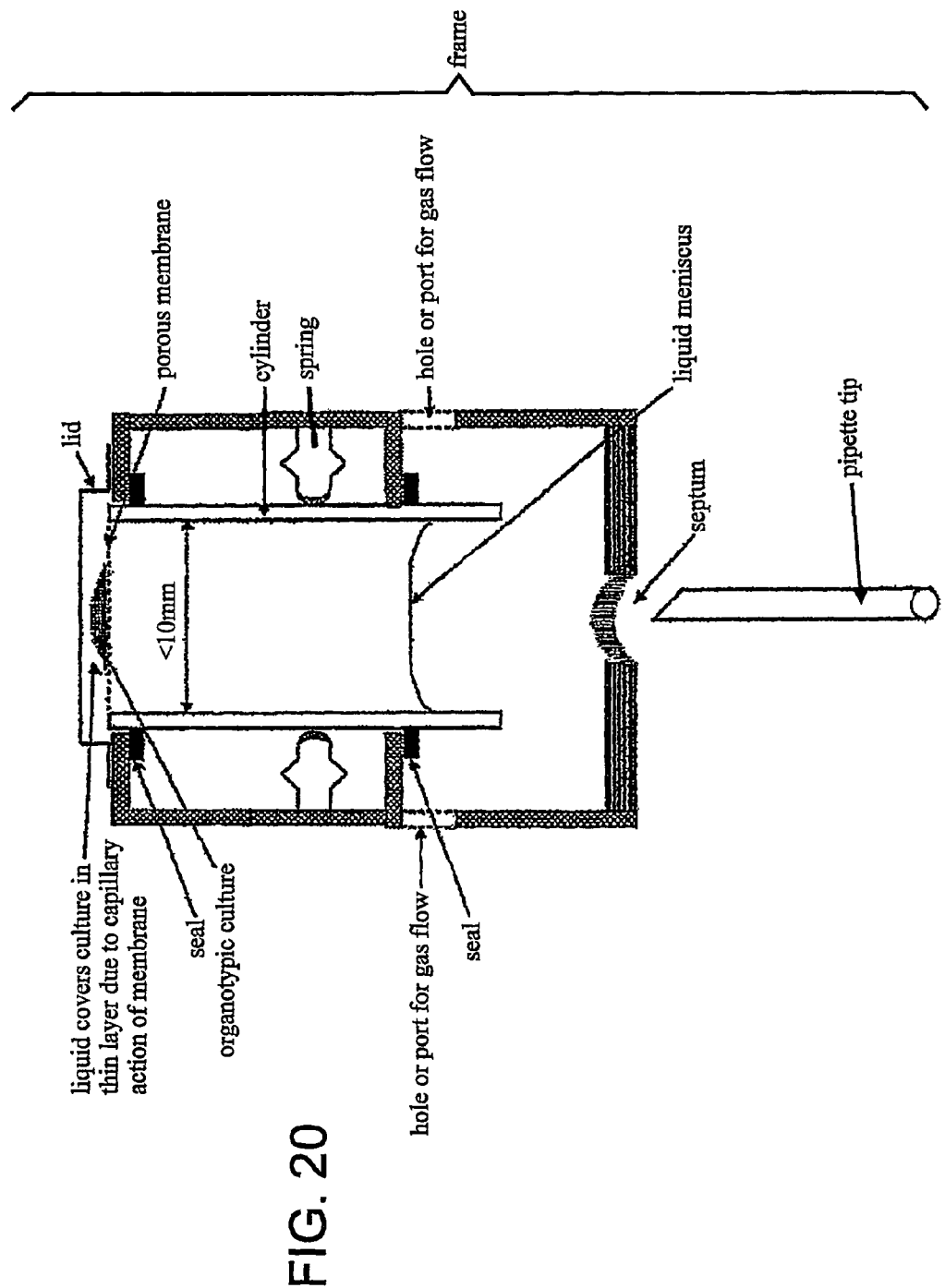

FIG. 20: Cross-section of a modified device for organotypic culture with additional components holding the conduit in place.

EXAMPLES

Example 1

Organotypic Culture of Dissociated Cells from Mouse Embryos Cortex (E-18)

Embryonic brains were removed from mouse embryos, and the two hemispheres were separated. After removal of the cerebellum as well as the thalamus and basal ganglia, the pia mater was carefully removed and cortical regions from 5 brains were digested with 0.1% trypsin in Hepes buffered salt solution (HBSS). Clumps of cells were allowed to settle under gravity, and overlying dissociated cells in suspension were gently aspirated with a pipette and placed in a fresh centrifuge tube.

Dissociated cells were compacted by spinning at 1000×g for 10 minutes, and 2-5 µl of the resulting cell pellet was removed directly with a sterile pipette tip and placed on the centre of the Biopore hydrophilic PTFE membrane of a Millipore-CM culture device.

Cortical culture medium (10% Ham's F12 (Sigma), 8% FBS, 2% Horse serum, 10 mM Hepes (Gibco), 2 mM L-Glutamine (Gibco), 50 Units Pen/strep made up to 1× media in DMEM(+glucose) was added to the underside of the membrane. Other media containing serum can also be used. The culture compacted further through equilibration of the liquid level by capillarity.

A typical culture made according to the invention from dissociated mouse cortical cells is shown in FIG. 1. The culture does not show the gross anatomical features that are typical of slice cultures, but has a uniform surface. Within 3-5 days and for at least 5 weeks these cultures show organotypic features. For example, the existence of appropriate cell types can be demonstrated by staining with labelled antibodies that recognise cell type-specific antigens. The use of three such antibodies to stain a typical culture made according to the invention from dissociated mouse cortical cells is shown in FIG. 2. FIG. 2A shows active cholinergic neurons stained with goat anti-choline acetyltransferase supplied by Chemicon (catalogue code AB144P), used at 1:100 dilution. The goat antibody was detected with Cy3-conjugated affinity-purified donkey anti-goat IgG antibody (Jackson ImmunoResearch Laboratories, Inc). FIG. 2B shows astrocytes detected with rabbit anti-glial fibrillary acidic protein (GFAP) antibody from Sigma (catalogue code G9269), used at 1:200 dilution. The rabbit antibody was detected with Alexa Fluor™ 568-labelled goat anti-rabbit IgG antibody (Molecular Probes, Invitrogen). FIG. 2C shows neurons expressing the neuron-specific beta tubulin III, detected with Covance monoclonal anti-beta tubulin III antibody (catalogue code MMS-435P) used at 1:200 dilution. The mouse monoclonal antibody was detected with Alexa Fluor™ 488-labelled goat anti-mouse IgG antibody (Molecular Probes, Invitrogen). These images demonstrate that even after 5 weeks in culture healthy functioning neurons were present and labelling of both neurons and astrocytes showed appropriate astrocyte-neuronal connections. Glial cells would have dominated the culture after a few days if the culture was not organotypic. A culture made according to the invention using dissociated cells shows interneuronal connections that are typical of organotypic brain cultures but are not found when dissociated cells are cultured by other procedures.

Further evidence of organotypic activity is shown by the electrophysiological activity of the culture. The organotypic culture was overlaid with a multi-electrode array (M.E.A.), shown in FIG. 3, which is an electrophysiological device that is commonly used with organotypic slice cultures. A suitable M.E.A. that is integrated into the membrane has been described by the present inventor in EP1133691 and U.S. Pat. No. 6,689,594. This device does not interfere with the compaction of the cells.

Spontaneous activities as well as Evoked Field Potentials can be recorded from the different electrodes of the M.E.A. Such spontaneous electrophysiological activity in a cortical culture produced according to the method described above is shown in FIG. 4. The effect of the culture on a potential difference applied between any pair of electrodes can also be measured using the M.E.A. The electrophysiological activity invoked in a cortical culture produced according to the method described above is shown in FIG. 5. These patterns of evoked potentials are typical of brain organotypic cultures, and indicate that the cultures made according to the method invention surprisingly have the characteristics typical of organotypic cultures. Such dissociated cells or numerous explants or microexplants are capable of high throughput culture whereas organotypic slice cultures are not suitable for high throughput applications.

In a further experiment recorded, two identical cultures prepared as described above from dissociated cells from mouse cortex were placed on the same Biopore hydrophilic PTFE membrane separated by a space 3 mm wide. The arrangement of the cultures is shown schematically in FIG. 6. An example of two such adjacent cultures is shown in FIG. 7 with a spot of hydrogel (BD™ PuraMatrix™ Peptide Hydrogel, BD Biosciences catalogue number 354250) placed between the two cultures. BD Biosciences Matrigel™ or agarose can also be used in place of PuraMatrix™ hydrogel. In this case cortex from THY-1 GFP transgenic mice (Feng G. et al 2000) was used because neurons from these mice express green fluorescent protein and can be imaged directly. FIG. 7 shows that a culture made according to the invention using dissociated cells from mouse cortex can grow axons beyond the boundaries of the culture towards a second culture placed on the same porous membrane. Axonal processes extended in both directions due to the diffusion of chemotactic signals and new neuronal connections were formed between the cultures. An M.E.A. of the design illustrated in FIG. 8 was used to demonstrate the integrity of neuronal connections. Furthermore, the integrity of neuronal connections has been demonstrated in the same cultures before and after international air travel, showing the stability and usefulness of the method of the invention.

A further demonstration of the usefulness and flexibility of the method of the invention is afforded by the data shown in FIG. 9. Dissociated cells can be frozen and stored by well-established procedures prior to organotypic culture by the method of the invention. FIG. 9 shows electrophysiological responses of a culture made according to the invention from frozen and thawed dissociated cells from mouse cortex. The paired-pulse evoked field potentials shown in FIG. 9A and the spontaneous activities shown in FIG. 9B are typical of other organotypic brain cultures made according to the invention, and of organotypic brain slice cultures.

The high reproducibility of the culture method of the invention is illustrated by the small variation in protein concentration between different cultures shown in FIG. 10. Protein concentration was measured by the BCA assay (Smith P. et al. 1985).

We have also demonstrated the growth and differentiation of mouse neuronal stem cells in co-culture according to the invention with dissociated cells from mouse cortex. Other co-culture examples include the differentiation of macrophages to microglia when co-cultured organotypically with dissociated brain cells according to the invention.

Example 2

Organotypic Culture of Dissociated Cells from Rat Heart

Dissociated neonatal rat ventricular myocytes were isolated as described by Ren et al (1998). Briefly, the animals were euthanized, and their hearts were rapidly removed and perfused with oxygenated Krebs-Henseleit bicarbonate (KHB) buffer. Hearts were subsequently perfused with a nominally $Ca^{2+}$-free KHB buffer for 2 to 3 minutes until spontaneous contractions ceased, followed by a 20-minute perfusion with $Ca^{2+}$-free KHB containing 0.5% w/v type II collagenase (Invitrogen catalogue number 17101) and 0.1 mg/mL hyaluronidase (Sigma-Aldrich catalogue number H 4272). After perfusion, the left ventricle was removed, minced, and incubated with fresh enzyme solution ($Ca^{2+}$-free KHB containing 0.5% w/v type II collagenase) for 3 to 5 minutes. The cells were further digested with 0.2% trypsin before being filtered through a nylon mesh (300 μm). Clumps of cells were allowed to settle under gravity, and overlying dissociated cells in suspension were gently aspirated with a pipette and placed in a fresh centrifuge tube.

Dissociated cells were compacted by spinning at 1000×g for 10 minutes, and 2-5 μl of the resulting cell pellet was removed directly with a sterile pipette tip and placed on the centre of the Biopore hydrophilic PTFE membrane of a Millipore-CM culture device.

Neurobasal medium (Invitrogen catalogue number 21103-049) supplemented with Gibco (Invitrogen catalogue number 17504-044) was added to the underside of the membrane. The culture was compacted further through equilibration of the liquid level by capillarity.

The resulting culture does not show the gross anatomical features that are typical of slice cultures, but has a uniform surface. Within 10 days, these cultures show organotypic features. FIG. 11 shows spontaneous rhythmic electrophysiological activity that is comparable to the beating of a heart. The beating rate shown is 1 beat per 2.6 seconds which is typical of beating activity achieved by others in cultures of cardiomyocytes in the absence of innervation. In the case of the present invention however, unlike previous methods for dissociated cell culture, the organotypic features of the culture are stable for several weeks or several months, not the 3-5 days that is typical for other cultures of dissociated cells. The long organotypic culture stability that is achieved by the present invention allows experiments with stable expression of transgenes and siRNA and the measurement of drug response over a long time-course in screening experiments, whereas other dissociated cell cultures are stable only for a few days and are no longer organotypic when stable transgene expression is optimal.

Example 3

Organotypic Culture of Dissociated Cells from Human Heart

Dissociated human foetal cardiomyocytes were isolated as described by Mummery C. et al (2002), from tissue provided under license by the University of Southampton. Briefly, foetal atrium or ventricle was macerated and digested with 0.2% trypsin before being filtered through a nylon mesh (300 μm). Clumps of cells were allowed to settle under gravity, and overlying dissociated cells in suspension were gently aspirated with a pipette and placed in a fresh centrifuge tube. Dissociated cells were compacted by spinning at 1000×g for 5 minutes, and 5-10 μl of the resulting cell pellet was removed directly with a sterile pipette tip and placed on the centre of the Biopore hydrophilic PTFE membrane of a Millipore-CM culture device. Neurobasal medium (Invitrogen catalogue number 21103-049) supplemented with Gibco (Invitrogen catalogue number 17504-044) was added to the underside of the membrane. The culture was compacted further through equilibration of the liquid level by capillarity.

As in Example 2, beating cultures were established within 10 days. In the case of atrial cultures, the beating rate was 140-150 beats per minute. Vetricular cultures beat more slowly at about 30 beats per minute. This example demonstrates that the method of the invention is not specific to rodent organs, and other examples illustrate its application to a range of tissues.

Example 4

Organotypic Culture of Dissociated Cells from Mouse Embryos Liver (E-16-18)

Embryonic livers were removed from mouse embryos and placed in ice cold Phosphate Buffered Saline. The liver was then chopped into smaller pieces using a scalpel and then transferred into Earle's Balanced Salts Solution (EBSS) warmed to 37° C. The liver pieces were then triturated with 3 flame-polished Pasteur pipettes, with apertures of decreasing sizes to produce a cell suspension. Clumps of cells were allowed to settle under gravity, and overlying dissociated cells in suspension were gently aspirated with a pipette and placed in a fresh centrifuge tube. Dissociated cells were compacted by centrifuging at 1500×g for 3 minutes. The remaining pellet was then resuspended to a concentration of approximately 20,000 cells per µl and 5-10 µl of the resulting cell pellet was removed directly with a sterile pipette tip and placed on the centre of the Biopore hydrophilic PTFE membrane of a Millipore-CM culture device. Liver culture medium (Verrill C. et al (2002)) was added to the underside of the membrane. The culture compacted further through equilibration of the liquid level by capillarity. The liver cultures were maintained in vitro for at least 10-days.

FIG. 12 shows staining of a mouse embryonic liver culture made according to the invention with monoclonal anti-smooth muscle alpha actin (SMA) antibody clone 1A4 purified mouse Immunoglobulin. Bound antibody was detected with AlexaFluorm488-labelled goat anti-mouse IgG antibody (Molecular Probes, Invitrogen). SMA is present in activated hepatic stellate cells and provides a marker for active liver regeneration. Liver cultures generated by the method of the invention behave organotypically. This provides very considerable advantages for high-throughput drug development assays using liver cells. The ability afforded by the invention to create organotypic cultures from dissociated liver cells, which can be obtained in large quantities, enables high-throughput assays to be developed easily, and organotypic cultures with appropriate intercellular connections are more reliable indicators of in vivo responses to drugs or toxins than are assays with non-organotypically cultured dissociated cells. Organotypic liver cultures are a major commercial opportunity due to the crucial role of the liver in drug metabolism and toxicity.

Example 5

Organotypic Culture of Dissociated Cells from Human Pancreas

Dissociated cells from human foetal pancreas were isolated as described by Turnpenny L. et al (2003). Briefly, foetal pancreas was digested with 0.2% trypsin before being filtered through a nylon mesh (300 µm). Clumps of cells were allowed to settle under gravity, and overlying dissociated cells in suspension were gently aspirated with a pipette and placed in a fresh centrifuge tube. Dissociated cells were compacted by centrifuging at 1000×g for 5 minutes, and 5-10 µl of the resulting cell pellet was removed directly with a sterile pipette tip and placed on the centre of the Biopore hydrophilic PTFE membrane of a Millipore-CM culture device. Neurobasal medium (Invitrogen catalogue number 21103-049) supplemented with Gibco (Invitrogen catalogue number 17504-044) was added to the underside of the membrane. The culture was compacted further through equilibration of the liquid level by capillarity.

FIG. 13 demonstrates that the method of the invention generates an organotypic culture from dissociated pancreatic cells that retains critical features of the pancreas in vivo. After 11 days in culture, staining with anti-insulin antibody (FIG. 13B) showed the insulin expression characteristic of the pancreas. Pancreatic development is accompanied by expression of the SOX9 homeodomain transcription factor (Piper K. et al 2002). Expression of SOX9 in the organotypic pancreatic culture made according to the invention was revealed by anti-SOX9 antibody (polyclonal rabbit anti-SOX9 antibody from Chemicon, detected by biotin-labelled (biotinylated) anti-rabbit followed by streptavidin-Texas Red, both from Vector Labs), as shown in FIG. 13C. FIG. 13D shows cell nuclei stained with DAPI.

Example 6

Organotypic Culture of Transfected Dissociated Cells from Mouse Brain

A key feature of the method of the invention is the ability to introduce genes for over-expression or siRNA for the ablation of expression into dissociated cells prior to the generation of organotypic cultures. The introduction of transgenes or siRNA is more efficient in dissociated cells than in organotypic slice cultures because the whole surface of each dissociated cell is accessible to the lipophilic complex or viral vector used for introduction. FIG. 14 shows an organotypic culture generated from dissociated cells from P0 mouse brain. The cells were transduced with the gene for Enhanced green Fluorescent Protein (EGFP) immediately prior to culturing.

Neonatal brains were removed, and the two hemispheres were separated. After removal of the cerebellum as well as the thalamus and basal ganglia, the pia mater was carefully removed and cortical regions from brains were digested with 0.2% trypsin in Hepes buffered salt solution (HBSS). Clumps of cells were allowed to settle under gravity, and overlying dissociated cells in suspension were gently aspirated with a pipette and placed in a fresh centrifuge tube. Dissociated cells were compacted by spinning at 1000×g for 5 minutes, and 5 µl of the resulting cell pellet was removed directly with a sterile pipette tip. 2 µl of lentiviral construct rHIV1-cPPT-SYN1-GFP-WPRE encapsulated with vesicular stomatitis virus serotype G (VSVG) envelope at a concentration of $1.8^{11}$ physical particles per ml was added to each 5 µl of centrifuged preparation prior to placing on the centre of the Biopore hydrophilic PTFE membrane of a Millipore-CM culture device. Cortical culture medium (10% Ham's F12 (Sigma), 8% FBS, 2% Horse serum, 10 mM Hepes (Gibco), 2 mM L-Glutamine (Gibco), 50 Units Pen/strep made up to 1× media in DMEM(+glucose) was added to the underside of the membrane. The culture compacted further through equilibration of the liquid level by capillarity. Digital images were captured 7 days later.

Example 7

Devices for Organotypic Culture

As shown in FIG. 15, a preferred device of the invention comprises a cylinder and a porous membrane glued or heat-sealed or ultrasonically sealed to one end of the cylinder, and a frame which holds the cylinder vertically and creates a chamber surrounding the open end of the cylinder.

The cylinder contains a volume of liquid culture medium which is retained by capillarity in the cylinder so that it is in contact with the lower surface of the porous membrane. The liquid meniscus of the volume of liquid medium is shown.

The device further comprises a lid which encloses the membrane-sealed end of the vessel and provides for control of the atmosphere surrounding the organotypic culture, in that gaseous exchange is possible, but microbial contamination is prevented.

As shown in FIGS. 16 and 17, a further preferred device of the invention comprises a modification of the device of FIG. 15, such that an additional cylinder is sealed to the porous membrane on the contralateral side of the porous membrane to the cylinder shown in FIG. 15. As shown in the schematic description of this aspect of the method of the invention in FIG. 16, the additional cylinder is used as a conduit to contain the cell suspension immediately prior to and during compaction. Subsequent to compaction for example by centrifugation or aspiration, the cylinder used to contain the cell suspension may be removed or left in place. If it is left in place it is covered with a lid during culture to provide for control of the atmosphere surrounding the organotypic culture. The cylinder not used to contain the cell suspension is used following centrifugation to contain a volume of liquid culture medium which is retained by capillarity. The cylinder used to contain the cell suspension may be of smaller internal cross-section than the cylinder used to contain the liquid culture medium to ensure that the whole area of the culture is accessed by culture medium through the porous membrane. The cylinder used to contain the cell suspension is designed to ensure that the said cylinder is adequately supported and the said cylinder does not damage the porous membrane under the influence of a gravitational field. For example the difference in size between the external cross-section of the said cylinder and its internal cross section is sufficient for the weight of the said cylinder to be fully supported by the frame of the device during centrifugation.

In the case of an assembly of devices for high throughput the lid preferably would cover the whole assembly. The lid may be loose-fitting to allow gas diffusion, having a skirt that overlaps the edges of the assembly to minimise contamination in the presence of slight air turbulence. It is well known by practitioners of tissue culture that air turbulence should be minimised. Alternatively, the lid may be tight fitting in which case ports may be provided in the frame so that gas can circulate between the chambers and the space between the lid and the membrane.

The chamber preferably comprises a pre-fabricated plastic shape incorporating two sealing rings which positions the chamber firmly around the base of the cylinder. Preferably, the seals are sealing rings fabricated of neoprene that form a gas-tight seal around the base of the cylinder.

The base of the chamber further comprises a septum which can be penetrated by a pipette to facilitate change of the medium in the chamber without exposing the medium to the surrounding environment.

The interior of the chamber preferably is accessible for gas diffusion or perfusion and the chamber comprises two holes or ports for gas flow to control atmospheric conditions. The chamber and the frame preferably comprise additional ports to allow gas flow between the chamber and the space above the membrane covered by a lid.

As shown in FIGS. 18 and 19, a preferred high-throughput device for multiple organotypic cultures according to the invention comprises multiple devices for a single organotypic culture shown in FIGS. 15 and 17. Each cylinder in the high-throughput device contains its own supply of liquid medium retained in contact with the membrane by capillarity. The chambers at the base of the cylinders are, however, in communication and gas flow between the chambers is possible, thereby allowing the control of atmospheric conditions in all the chambers through the gas flow ports at either end of the device. Furthermore, the space between the lid and the culture is made contiguous with the chambers by means of ports in the frame, thereby allowing control of the atmospheric conditions surrounding the cultures on the membranes.

As shown in FIG. 19, a single insert accessory may comprise multiple removable conduits for a high throughput device to contain the cell suspension prior to and during compaction. There may be 1 or several such removable conduits for each fixed conduit used to contain the liquid culture medium. In the example shown there are 4 such removable conduits for each fixed conduit.

As shown in FIG. 20, the devices of FIGS. 15 and 17 may comprise further elements that hold the conduits in place relative to the frame such as, for example, springs between the conduits and the frame.

REFERENCES

Becker-Hapak M. et al, 2001, Methods Vol 24 pp 247-56. TAT-mediated protein transduction into mammalian cells.

Buchs P. et al, 1993, Brain Res. Dev. Brain. Res. Vol 71 pp 81-91, Structural modifications associated with synaptic development in area CA1 of rat hippocampal organotypic cultures Corradino R., 1973, J. Cell Biol., Vol 58, pp 64-78, Embryonic chick intestine in organ culture. A unique system for the study of the intestinal calcium absorptive mechanism.

Feng G. et al, 2000, Neuron, Vol 28, pp 41-51, Imaging neuronal subsets in transgenic mice expressing multiple spectral variants of GFP.

Giehl, 2002, EP1205541, Procedure for the long-term cultivation of organotypic slices of brain and other postnatal tissues, in particular of adult mammals.

Herlyn M., 2004, United States Patent Application 20040175367, Organotypic intestinal culture and methods of use thereof.

Honegger, P., and Monnet-Tschudi, F., 2001, Aggregating Neural Cell Cultures, pp 199-218 in Protocols for Neural Cell Culture (Fedoroff, S., and Richardson, A., eds) Third Edition, Humana Press, Totowa, N.J., USA, ISBN 1-59259-207-4).

Kalabis J. et al, (2003), FASEB J. vol 17, pp 1115-7, Stimulation of human colonic epithelial cells by leukemia inhibitory factor is dependent on collagen-embedded fibroblasts in organotypic culture.

Michalopoulos G. et al, 2001, Am J. Pathol. vol 159 pp 1877-87, Histological organization in hepatocyte organoid cultures Michalopoulos G. and Bowen W., 2004, United States Patent Application 20040151729, Novel long-term three-dimensional culture system.

Muller et al (2001) Protocols for Neural Cell Culture, 3rd Ed. pp 13-27, S. Fedoroff and A. Richardson eds, Humana Press, Inc., Totowa, N.J. Interface Organotypic Hippocampal Slice Cultures.

Mummery C. et al (2002), J. Anat. vol 200 pp 233-42, Cardiomyocyte differentiation of mouse and human embryonic stem cells.

Piper K (2002), Mech. Dev., Vol 116 pp 223-6. Novel SOX9 expression during human pancreas development correlates to abnormalities in Campomelic dysplasia.

Ren et al (1998) Am J. Physiol. vol 275 ppH 823-H830 Altered inotropic response to insulin-like growth factor I in diabetic rat heart: influence of intracellular Ca2+ and nitric oxide Rochkind S. et al, 2002, Neurol Res. vol 24 pp 355-60. Transplantation of embryonal spinal cord nerve cells cultured on biodegradable microcarriers followed by low power laser irradiation for the treatment of traumatic paraplegia in rats.

Shahar A. et al, 2001, European patent application EP1073420, Specially devised neuronal implants for reconstruction of damaged central nervous system.

Smith P. et al, 1985, Anal. Biochem. vol 150 pp 76-85, Measurement of protein using bicinchoninic acid.

Stoppini L. et al, 1991, Neurosci. Methods, Vol 37 pp 173-82, A simple method for organotypic cultures of nervous tissue.

Stoppini L et al, 1993, Neuroscience, Vol 57, pp 985-94, Lesion-induced neurite sprouting and synapse formation in hippocampal organotypic cultures.

Tumpenny L et al, 2003, Stem Cells, Vol 21 pp 598-609. Derivation of human embryonic germ cells: an alternative source of pluripotent stem cells.

Verrill C et al, 2002, J Pharmacol Toxicol Methods, Vol48 pp 103-10. Organotypic liver culture in a fluid-air interface using slices of neonatal rat and adult human tissue—a model of fibrosis in vitro.

Wicks W., 1968, J. Biol. Chem., Vol 243, pp 900-6, Induction of tyrosine-alpha-ketoglutarate transaminase in fetal rat liver.

Wildenthal K., 1971, J. Appl. Physiol., Vol 30, pp 153-7, Long-term maintenance of spontaneously beating mouse hearts in organ culture.

Wille J., 1998, U.S. Pat. No. 5,834,312, Process and media for the growth of human epithelia.

The invention claimed is:

1. A method of producing an organotypic culture, the method comprising
compacting dissociated cells from an organ, in suspension, on one surface of a porous membrane by capillarity exerted by a liquid medium supplied on a contralateral surface of the membrane and retained in contact with the contralateral surface of the membrane, wherein the cells are compacted to achieve greater than 5% close packing, wherein the approximate degree of close packing is calculated using the formula $$\text{Degree of close packing} = (N_e \times V_e / V_{cm}) \times 100\% \quad \text{(Formula 1)}$$

where
$N_e$ is the number of cells,
$V_e$ is the average volume of the cells, and
$V_{cm}$ is the measured volume of the total volume of the cell mass in the culture.

2. A method according to claim 1, wherein said cells are compacted to achieve greater than 10% close packing.

3. A method according to claim 1, wherein the cells are compacted by a compactive force of less than $2 \times 10^{-3}$ dyne per cell.

4. A method according to claim 3, wherein the cells are compacted by a force of between $10^{-5}$ dyne per cell and $5 \times 10^{-4}$ dyne per cell.

5. A method of producing an organotypic culture, the method comprising compacting cells which are microexplants from an organ, in suspension, on one surface of a porous membrane by capillarity exerted by liquid medium supplied on a contralateral surface of the membrane and retained in contact with the contralateral surface of the membrane, wherein the microexplants are compacted to achieve greater than 5% close packing, wherein the approximate degree of close packing is calculated using the formula $$\text{Degree of close packing} = ((N_{nc} \times V_{nc} \times P_{nc}) / ((N_{nc} \times V_{nc} \times P_{nc}) + (V_{cm} - (N_e \times V_e)))) \times 100\% \quad \text{(Formula 2)}$$

where $N_{nc}$ is the number of cells that are capable of making new contacts,
$V_{nc}$ is the average volume of the cells in the culture that are capable of making new contacts,
$P_{nc}$ is the average proportion of the surface area of the cells that are capable of making new contacts that is actually available for making new contacts,
$V_{cm}$ is the measured total volume of the cell mass in the culture,
$N_e$ is the number of microexplants in the culture and
$V_e$ is the average volume of the microexplants in the culture.

6. A method according to claim 1, further comprising the preliminary step of isolating the cells from the organ.

7. A method according to claim 1, wherein said organ is a mammalian organ.

8. A method according to claim 7, wherein said organ is a central nervous system organ, bone marrow, spleen, thymus, heart, mammary glands, liver, pancreas, thyroid, skeletal muscle, kidney, lung, intestine, ovary, bladder, testis or uterus.

9. A method according to claim 8, wherein said organ is the central nervous system organ, heart, liver or pancreas.

10. A method according to claim 9, wherein the organ is the central nervous system organ.

11. A method according to claim 10, wherein the organ is brain.

12. A method according to claim 1, wherein said cells are stem cells.

13. A method according to claim 1, wherein the cells are from more than one organ.

14. A method according to claim 1, wherein the cells are from a healthy organ or organs.

15. A method according to claim 1, wherein the cells are from a diseased organ or organs.

16. A method according to claim 1, wherein the cells have been genetically altered.

17. A method according to claim 1, wherein the cells are from a transgenic animal organ.

18. A method according to claim 1, wherein the membrane is optically transparent.

19. A method according to claim 1, further comprising cryopreserving the resulting organotypic culture.

20. A high-throughput method for the preparation of a collection of organotypic cultures comprising preparing multiple organotypic cultures according to the method of claim 1 in parallel.

21. A method according to claim 1, wherein said cells are compacted to achieve greater than 20% close packing.

22. A method according to claim 1, wherein said cells are compacted to achieve greater than 30% close packing.

23. A method according to claim 1, wherein said cells are compacted to achieve greater than 40% close packing.

24. A method according to claim 1, wherein said cells are compacted to achieve greater than 50% close packing.

25. A method according to claim 1, wherein said organ is a human organ.

26. A method according to claim 1, wherein the organotypic culture comprises monocytes.

27. A method according to claim 5, wherein said cells are compacted to achieve greater than 20% close packing.

28. A method according to claim 5, wherein said cells are compacted to achieve greater than 30% close packing.

29. A method according to claim 5, wherein said cells are compacted to achieve greater than 40% close packing.

30. A method according to claim 5, wherein said cells are compacted to achieve greater than 50% close packing.

31. A method according to claim 5, wherein said organ is a human organ.

32. A method according to claim 5, wherein the organotypic culture comprises monocytes.

33. A method of producing an organotypic culture, the method comprising, compacting dissociated cells from connective tissue, in suspension, on one surface of a porous membrane by capillarity exerted by liquid medium supplied on a contralateral surface of the membrane and retained in contact with the contralateral surface of the membrane, wherein the microexplants are compacted to achieve greater than 5% close packing, wherein the approximate degree of close packing is calculated using the formula $$\text{Degree of close packing} = (N_e \times V_e / V_{cm}) \times 100\% \quad \text{Formula 1}$$

where
- $N_e$ is the number of cells,
- $V_e$ is the average volume of the cells, and
- $V_{cm}$ is the measured volume of the total volume of the cell mass in the culture.

34. A method according to claim 1, wherein the organotypic culture comprises blood cells.

35. A method according to claim 5, wherein said organ is a central nervous system organ, bone marrow, spleen, thymus, heart, mammary glands, liver, pancreas, thyroid, skeletal muscle, kidney, lung, intestine, ovary, bladder, testis or uterus.

36. A method of producing an organotypic culture, the method comprising compacting cells which are microexplants from connective tissue, in suspension, on one surface of a porous membrane by capillarity exerted by liquid medium supplied on a contralateral surface of the membrane and retained in contact with the contralateral surface of the membrane, wherein the microexplants are compacted to achieve greater than 5% close packing, wherein the approximate degree of close packing is calculated using the formula $$\text{Degree of close packing} = ((N_{nc} \times V_{nc} \times P_{nc}) / ((N_{nc} \times V_{nc} \times P_{nc}) + (V_{cm} - (N_e \times V_e)))) \times 100\% \quad \text{(Formula 2)}$$

where $N_{nc}$ is the number of cells that are capable of making new contacts,
- $V_{nc}$ is the average volume of the cells in the culture that are capable of making new contacts,
- $P_{nc}$ is the average proportion of the surface area of the cells that are capable of making new contacts that is actually available for making new contacts,
- $V_{cm}$ is the measured total volume of the cell mass in the culture,
- $N_e$ is the number of microexplants in the culture and
- $V_e$ is the average volume of the microexplants in the culture.

37. A method according to claim 5, wherein the organotypic culture comprises blood cells.

\* \* \* \* \*